(12) United States Patent
Oud et al.

(10) Patent No.: US 11,162,034 B2
(45) Date of Patent: Nov. 2, 2021

(54) CRACKING FURNACE

(71) Applicant: Technip France S.A.S., Courbevoie (FR)

(72) Inventors: Peter Oud, Zoetermeer (NL); Esmaeil Mahmoudi Namarvar, Zoetermeer (NL); Marco Van Goethem, Zoetermeer (NL)

(73) Assignee: TECHNIP FRANCE S.A.S., Courbevoie (FR)

( * ) Notice: Subject to any disclaimer, the term of this patent is extended or adjusted under 35 U.S.C. 154(b) by 0 days.

(21) Appl. No.: 16/313,356

(22) PCT Filed: Jun. 30, 2017

(86) PCT No.: PCT/EP2017/066331
§ 371 (c)(1),
(2) Date: Dec. 26, 2018

(87) PCT Pub. No.: WO2018/002330
PCT Pub. Date: Jan. 4, 2018

(65) Prior Publication Data
US 2019/0144759 A1    May 16, 2019

(30) Foreign Application Priority Data
Jul. 1, 2016  (GB) ...................................... 1611573

(51) Int. Cl.
*C10G 9/20* (2006.01)
*C10G 9/00* (2006.01)
*C07C 4/04* (2006.01)

(52) U.S. Cl.
CPC .................. *C10G 9/20* (2013.01); *C07C 4/04* (2013.01); *C10G 9/007* (2013.01); *C10G 2400/20* (2013.01)

(58) Field of Classification Search
CPC ...... C10G 9/20; C10G 9/203; C10G 2400/20; C10G 9/007; B01J 19/243; B01J 2219/00157; B01J 6/008
See application file for complete search history.

(56) References Cited

U.S. PATENT DOCUMENTS

| 1,818,082 A | 8/1931 | Mott | |
| 2003/0127361 A1* | 7/2003 | Chae | ........................ C10G 9/20 208/130 |

(Continued)

FOREIGN PATENT DOCUMENTS

| CN | 101619943 A | 1/2010 |
| CN | 101619949 A | 1/2010 |

(Continued)

OTHER PUBLICATIONS

International Search Report and Written Opinion of International Application No. PCT/EP2017/066331 dated Sep. 29, 2017, 10 pages.

*Primary Examiner* — Sharon Pregler
(74) *Attorney, Agent, or Firm* — Fay Sharpe LLP

(57) ABSTRACT

A cracking furnace includes a pyrolysis tube 1 for carrying a flow of fluid, the pyrolysis tube including a radially inner body 3 and a radially outer wall 2 which together define an annular flow passage 5, wherein at least one of the radially inner body and the radially outer wall has a centre line which extends helically in a longitudinal direction of the pyrolysis tube, so as to promote rotation of the fluid as it flows along the pyrolysis tube.

20 Claims, 29 Drawing Sheets

(56) References Cited

U.S. PATENT DOCUMENTS

| | | | |
|---|---|---|---|
| 2004/0134557 A1* | 7/2004 | Cymbalisty | C10G 1/047 |
| | | | 138/177 |
| 2009/0095594 A1 | 4/2009 | Caro et al. | |
| 2014/0127091 A1 | 5/2014 | Wang et al. | |

FOREIGN PATENT DOCUMENTS

| | | |
|---|---|---|
| CN | 102095332 A | 6/2011 |
| EA | 014787 B1 | 2/2011 |
| JP | H09 292191 A | 11/1997 |
| JP | 2009270802 A | 11/2009 |
| JP | 2014519543 A | 8/2014 |
| RU | 2221835 C2 | 1/2004 |
| WO | WO 2005/068926 A1 | 7/2005 |
| WO | WO 2005/075607 A1 | 8/2005 |
| WO | WO 2006/032877 A1 | 3/2006 |
| WO | WO 2010/032024 A2 | 3/2010 |
| WO | WO2018002330 A1 | 1/2018 |

\* cited by examiner

CRACKING FURNACE

FIELD

The invention relates to a cracking furnace comprising a pyrolysis tube for carrying a flow of fluid, such as gas or liquid.

BACKGROUND

In an ethylene cracking furnace burners are provided in a firing box through which at least one pyrolysis tube passes whilst carrying a flow of hydrocarbon feedstock as a process gas. It is desirable in cracking furnaces that the hydrocarbon feedstock is converted as quickly as possible into the desired products, such as ethylene, propylene and butadiene. Low residence time in the pyrolysis tube at the highest possible temperature and at a hydrocarbon partial pressure as low as possible are the main parameters that determine the selectivity towards favourable products.

The inner surface of pyrolysis tubes in cracking furnaces are subject to coke formation and need to be de-coked at regular intervals once the pyrolysis tube end of run condition is reached. The end of run condition depends on the extent of coke build-up on the inner surface of the pyrolysis tube and can be limited by a maximum allowable pressure drop over the length of the pyrolysis tube, or by a maximum allowed pyrolysis tube metal temperature. Both pressure drop and pyrolysis tube metal temperature are increased by this coke deposition on the inner surface of the pyrolysis tube. Excessive pyrolysis tube metal temperatures are not desirable because operation of pyrolysis tubes close to their metallurgical limit results in creep and carburisation.

The rate of coke formation depends on feedstock conversion and temperature at the inner surface of the pyrolysis tube, where the coke is formed. The higher the feedstock conversion and the lower the temperature at the inner surface, the lower the coke formation.

It is known from WO 2005/068926 to increase the overall heat transfer from a pyrolysis tube to the fluid flowing along the tube by providing a cylindrical body inside the tube. This body receives radiation from the surrounding tube and transfers it to the fluid surrounding the body. The flow in this pyrolysis tube is predominantly axial, along the length of the tube.

It is known from WO 2006/032877 or WO 2010/032024 to provide a pyrolysis tube with a helical geometry which promotes swirling flow that reduces the thickness of the laminar layer at the inner surface of the tube and which promotes mass transfer from the inner wall into the central region of the tube, thereby increasing convective heat transfer away from the wall compared to that of a straight tube. This design has the added advantage that it increases the heat transfer with a minimum penalty with respect to additional pressure drop.

It is known from WO2005/075607 to provide a cracking furnace having a pyrolysis tube, which provides a dual pass of the flow through the cracking furnace. There are two upstream portions and then a reversal in the direction of flow as the two upstream portions feed into a common downstream portion.

SUMMARY

According to the invention there is provided a cracking furnace comprising a pyrolysis tube for carrying a flow of fluid, the pyrolysis tube comprising a radially inner body and a radially outer wall which together define an annular flow passage, wherein at least one of the radially inner body and the radially outer wall has a centre line which extends helically in a longitudinal direction of the pyrolysis tube so as to promote rotation of the fluid as it flows along the pyrolysis tube.

The promotion of rotation of the fluid flow in an annular flow passage improves heat transfer into the fluid. The rotational flow can result in the fluid having both a tangential and a radial velocity component on top of the axial velocity component, so-called swirl flow. The annular passage may therefore be considered, at least in the description of embodiments, as an annular swirl flow passage. The swirl flow in the annular passage improves the convective heat transfer, while the presence of the inner body creates the annular flow passage and increases the surface to volume ratio at the same time. It is possible to achieve a low residence time and improve the yield, i.e. the generation of the desired cracked products.

Examples of annular swirl flow passages include a first type of pyrolysis tube wherein both the radially inner body and the radially outer wall have respective centre lines which extend helically in a longitudinal direction of the pyrolysis tube, a second type in which the radially inner body has a straight centre line (or a centre line curved in one plane only) and the radially outer wall has a centre line which extends helically, and a third type in which the radially inner body has a centre line which extends helically and the radially outer wall has a straight centre line (or curves in one plane only).

Embodiments of the third type have the advantage that only the radially inner body has to be formed with a centre line which extends helically and the radially outer wall may be provided by a conventional tube. This makes it relatively inexpensive to manufacture.

The fluid may be a gas, as in the case of a cracking furnace for producing ethylene and/or other gaseous products, or it may be a liquid, as in the case of a visbreaker cracking furnace.

The pyrolysis tube may have an annular flow passage substantially along its full length in the cracking furnace, e.g. its full length through a furnace chamber or firebox of the cracking furnace.

In certain embodiments, the pyrolysis tube comprises a non-annular flow passage defined by a radially outer wall downstream of the annular flow passage. By providing the annular flow passage an improved heat flux to the fluid is obtained and pyrolysis starts earlier. However, at least in the case of cracking furnaces for producing ethylene or other gaseous products, due to a limited width of the annular area, this is at the expense of a lower capability to accommodate coke depositions and so results in a relative pressure drop increase compared to a non-annular flow passage in areas with high coke formation. Therefore, by providing a non-annular flow passage downstream of the annular flow passage the pressure drop increase as a result of increased coke formation is reduced and more cross-sectional area is made available to handle the increased coke depositions. In addition, in this downstream passage the concentration of desirable reaction products is increased and so is the tendency to produce by-products along with coke deposits by secondary reactions. It is beneficial in this region to have a low hydrocarbon partial pressure such that the concentration of the products and the corresponding reaction rate of the secondary reactions is as low as possible. All of this is achieved by a non-annular flow passage. Thus, the provision of a non-annular flow passage downstream of the annular flow passage makes available more cross-sectional area to accommodate a coke layer thickness and to minimize the influence of pressure drop on the yield of the desirable reaction products.

In embodiments, in a non-annular flow passage the whole cross-sectional area within the radially outer wall is available for flow. In other words, there is no radially inner body.

The pyrolysis tube may have an annular passage extending less than or equal to 75% of the length of the pyrolysis tube in the cracking furnace. In embodiments, the annular flow passage may extend less than or equal to 70% or 65% or 60% or 55% or 50% of the length of the pyrolysis tube in the cracking furnace. The remaining part of the pyrolysis tube in the cracking furnace may comprise a non-annular passage.

The non-annular flow passage may be defined by a radially outer wall which has a centre line which extends helically in a longitudinal direction of the pyrolysis tube. Alternatively, the non-annular flow passage may be defined by a radially outer wall which has a straight centre line (or is curved in a single plane only) in a longitudinal direction of the pyrolysis tube.

The radially outer wall of the annular flow passage may have an internal diameter which is greater than an internal diameter of the radially outer wall of the non-annular flow passage. This can help to reduce any tendency for the average axial flow velocity to decrease as the flow enters the non-annular flow passage. A transitional portion may be provided between the radially outer wall of the annular flow passage and that of the non-annular flow passage.

The pyrolysis tube may comprise a plurality of branches each having a respective radially inner body and a respective radially outer wall which together define a respective annular flow passage, at least one of the radially inner body and the radially outer wall of each branch being configured to promote rotation of the fluid flow, the branches joining together at a junction and the non-annular flow passage being provided downstream of the junction.

Such an arrangement may desirably increase the surface to volume ratio and promote rotation of the fluid flow in particular generating swirl flow, thereby improving heat transfer in the more upstream part of the pyrolysis tube where there is a plurality of branches. Further downstream, pressure drop may be minimised by providing the non-annular flow passage.

There may be two branches and the junction may then be a Y-junction.

In embodiments in which the pyrolysis tube comprises branches, the length of the annular passage in at least one of the branches may be less than or equal to 75% or 70% or 65% or 60% or 55% or 50% of the length of that branch plus the length of the pyrolysis tube extending downstream of the junction.

The pyrolysis tube may extend downwardly from an inlet thereto. Thus the flow of fluid along the pyrolysis tube may be in a downward direction. With the inlet at the top of the pyrolysis tube, any spalled coke does not block the inlet and may end up in a location where it may be combusted quickly during de-coking. This is irrespective of the number of tube passes (discussed further below).

The pyrolysis tube may have a single pass through a chamber of the cracking furnace. It may for example have an inlet at one end of the chamber and an outlet at the other end. Such an arrangement significantly reduces the residence time. In some single pass embodiments the pyrolysis tube extends downwardly from the inlet, whereby the passage of the flow of fluid along the pyrolysis tube is in a downward direction. This has the benefits discussed above in relation to spalled coke.

The pyrolysis tube may pass twice through a chamber of the cracking furnace, i.e. a dual pass pyrolysis tube. In these embodiments, the respective passes may be joined by a U-bend. This arrangement may be more attractive for cracking gaseous feedstock such as ethane and propane, which requires a longer residence time than cracking liquid feedstock such as naphtha and gas oil. For example, the pyrolysis tube may have an inlet and an outlet at an upper region of a chamber, with the flow of fluid being first downwardly in the first pass and then upwardly in the second pass.

In the single pass arrangement, there may be a non-annular flow passage downstream of an annular flow passage, for example in a top to bottom downward flow arrangement. In the dual pass arrangement, the first pass may include the annular flow passage, with the second pass including the non-annular flow passage.

In embodiments in which the pyrolysis tube provides a dual pass of flow through the cracking furnace, the pyrolysis tube may comprise an upstream portion in a first pass and a downstream portion in a second pass, and the downstream portion may at least to some extent be in the shadow of the upstream portion with respect to a burner of the cracking furnace. Thus, the upstream portion may be more exposed to radiant heat than the downstream portion with the advantage that the heat received on the outside of the downstream portion is more uniform. This can reduce peak temperatures in the wall of the pyrolysis tube in this downstream portion and hence reduce the tendency for the peak pyrolysis tube wall temperature to approach the metallurgical limit. This can prolong the period of time for which the furnace may be operated between de-coking procedures.

In the embodiments in which annular flow passage branches join, they may do so with the direction of flow generally remaining the same, for example a downward direction of flow. Thus, in a single pass arrangement, two branches each defining an annular flow passage may join at a Y-junction and then the flow may continue in the non-annular flow passage in the same general direction, e.g. downwardly.

In alternative arrangements the fluid flow in the plurality of branches may be generally parallel and in the same direction, e.g. downwardly, and the direction of fluid flow in the non-annular flow passage downstream of the junction at which the branches join may be in the opposite direction, e.g. upwardly. Thus a U-bend may be provided after the junction, or a plurality of U-bends may be provided, one for each branch, with the junction being provided downstream of the U-bends. In either case the non-annular flow passage may at least to some extent be in the shadow of at least one of the upstream branches with respect to a burner of the cracking furnace. Thus the branches with the annular flow passages are more exposed to radiant heat than the downstream non-annular flow passage with the advantage that the heat received on the outside of the downstream part is more uniform. As discussed above, this can reduce peak temperatures in the wall of the pyrolysis tube in this downstream part and hence reduce the tendency for the peak pyrolysis tube wall temperature to approach the metallurgical limit, thereby prolonging the period of time for which the furnace may be operated between de-coking procedures.

There are several options for the manner in which heat is provided to the cracking furnace. At least one burner may be provided in an upper region of a furnace chamber or in a bottom region of a furnace chamber or an intermediate region between top and bottom of a furnace chamber (i.e. side firing), or there may be any combination of the foregoing. In the case of solely top firing, the flue or exhaust gas may flow downwardly. In the case of a combination of top and side firing, the flue gas may flow downwardly. In the case of solely side firing, the flue gas may flow downwardly or upwardly. In the case of solely bottom firing, the flue gas may flow upwardly. In the case of a combination of bottom and side firing, the flue gas may flow upwardly.

In certain embodiments, the cracking furnace comprises at least one burner in a firing region of the cracking furnace where the pyrolysis tube extends, and the pyrolysis tube extends in the furnace downstream away from the firing region. In the case of a top firing furnace, the pyrolysis tube may extend in the furnace downstream and downwardly away from the firing region.

By maximising the heat flux to an upstream part of the pyrolysis tube, any coke is more evenly distributed over the tube inner surface, the tube material is utilised to its full potential and the inner body is used more effectively. As the fluid enters the pyrolysis tube at a lower temperature than when it exits, by providing the firing region at the upstream part of the pyrolysis tube, more margin is available up to the maximum tube skin temperature, allowing a higher heat flux. Moreover, if the annular flow passage is provided at an upstream part of the pyrolysis tube, when the outer tube temperature is raised by the at least one burner, then the radiative heat transfer from the radially outer wall to the inner body is increased. This improves the progression of the fluid temperature to the point where pyrolysis starts, raises the pyrolysis reaction conversion and increases the reaction temperature level improving the yield slate, i.e. the concentration in the output fluid of desirable reaction products.

The pyrolysis tube may extend downwardly from an inlet thereto. For example, the inlet to the pyrolysis tube may be at the top of a furnace chamber and an outlet may be at the bottom of the furnace chamber. Any spalled coke may fall down the tube away from the inlet and so does not then block the inlet and may end up in a location where it may be combusted quickly during de-coking.

In the case of downward flow of fluid in the pyrolysis tube, then top and/or side firing is beneficial.

The promotion of rotation of the fluid flow may be further improved by the radially inner body and/or the radially outer wall having at least one helical protuberance, such as a helical fin, protruding into the annular flow passage. For example, the radially inner body may have a main body provided with at least one helical protuberance to promote rotation of the fluid flow.

The annular passage may extend around the inner body substantially continuously and uninterrupted. Thus there may be no baffle or fin interrupting the annular passage as it extends circumferentially around the inner body.

In the embodiments in which both the radially inner body and the radially outer wall have respective centre lines which extend helically in a longitudinal direction of the pyrolysis tube, the axes of the helical rotation and the helical centre lines may be coincident. Thus, the helical centre lines may have the same pitch and amplitude and may be in phase.

In such arrangements, the width of the annular flow passage measured perpendicularly to the longitudinal direction of the pyrolysis tube will be the same at different circumferential points around the tube. This width is preferably less than or equal to 50% of the diameter of the radially outer wall, more preferably less than or equal to 40% or 35% or 30% or 25% of the diameter of the radially outer wall. It is beneficial if the gap between the inner body and the radially outer wall is made relatively small. This can reduce the temperature of the radially outer wall, because the average fluid velocity for a given flow rate is increased with smaller radial widths, and the heat transfer is correspondingly increased. However, the pressure drop is increased. The tube can then be designed to be limited by pressure drop rather than by tube metal temperature. By reducing tube metal temperatures, there is a reduction in creep and carburisation rate.

The width of the annular flow passage measured perpendicularly to the longitudinal direction of the pyrolysis tube may vary in the circumferential direction of the tube. The width may increase in the circumferential direction from a minimum on a first side of the inner body to a maximum on a second side diametrically opposite to the first side. The width may increase in the circumferential direction progressively from the first side to the second side. Continuing in the same circumferential direction, the width may decrease progressively from the second side to the first side.

A varying width of the annular flow passage measured perpendicularly to the longitudinal direction of the pyrolysis tube will occur for example for the second type of pyrolysis tube, in which the inner body has a straight centre line (or a centre line curved in a single plane) and the radially outer wall has a helical centre line. It will also occur for the third type of pyrolysis tube, in which the inner body has a helical centre line and the radially outer wall has a centre line which is straight (or is curved in a single plane).

In certain embodiments a maximum width of the annular flow passage measured perpendicularly to the longitudinal direction of the pyrolysis tube is less than or equal to the diameter of the radially outer tube, and may be less than or equal to half that diameter.

It is advantageous if the inner body has a relatively high emissivity. In effect, this means that it has a dull surface rather than a shiny surface. Such a dull surface is obtained where a coke layer forms on the surface.

At least one support may be provided to support the inner body in the pyrolysis tube. Longitudinally spaced apart supports may be provided. A first such support may be fixed to the radially outer wall and the inner body, and the second such support may comprise at least one support member fixed to the radially outer wall and positioned radially outwardly of the inner body but not fixed thereto. The first support may bear the weight of the inner body. The second support may assist in locating the inner body whilst allowing relative movement between the radially outer wall and the inner body. This is beneficial in the case of differential thermal movements and differential creep. The support member of the second support may be a ring positioned radially outwardly of the inner body but not fixed thereto. The support member may be fixed to the radially outer wall by radial ribs projecting radially inwardly from the outer wall to the support member.

The inner body may be prevented from touching the radially outer wall. It may be held in a generally central location to provide a consistent shape for the annular flow passage and for relatively even heat distribution.

The inner body may be solid or hollow.

In some embodiments, the inner body is a hollow body. This is lighter in weight than a solid body. Also, gas inside the hollow body can aid heat transfer from one part of the inner body to another, for example in vertical heat transfer from a lower hotter downstream part to a higher colder upstream part.

In other embodiments, for example for smaller diameter inner bodies, the inner body may be a solid body.

BRIEF DESCRIPTION OF THE DRAWINGS

Certain preferred embodiments of the invention will now be described by way of example and with reference to the accompanying drawings, in which.

DETAILED DESCRIPTION

Figure 1:
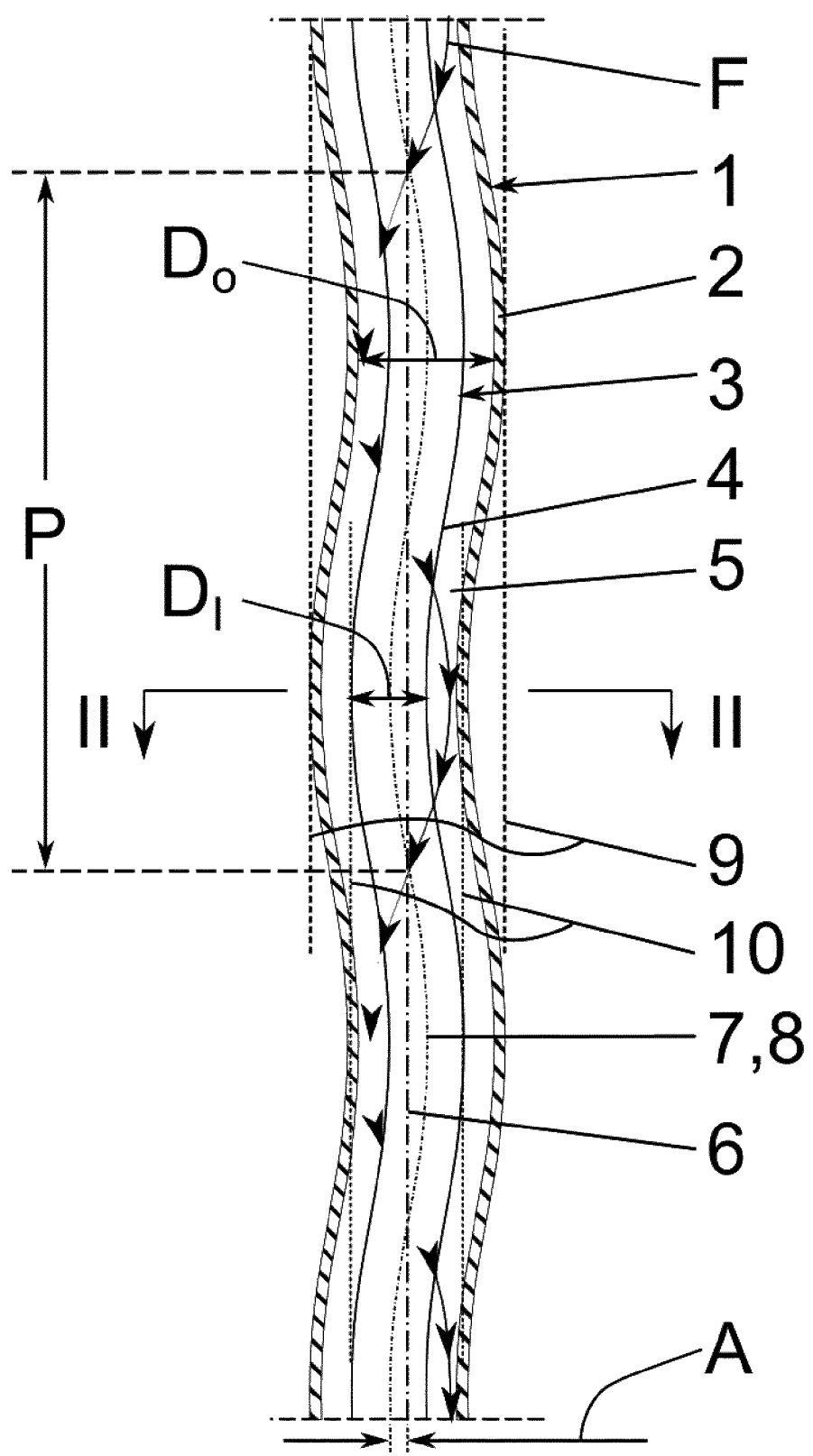
FIG. 1 is a schematic longitudinal sectional view of a portion of a first type of pyrolysis tube.
Figure 2:
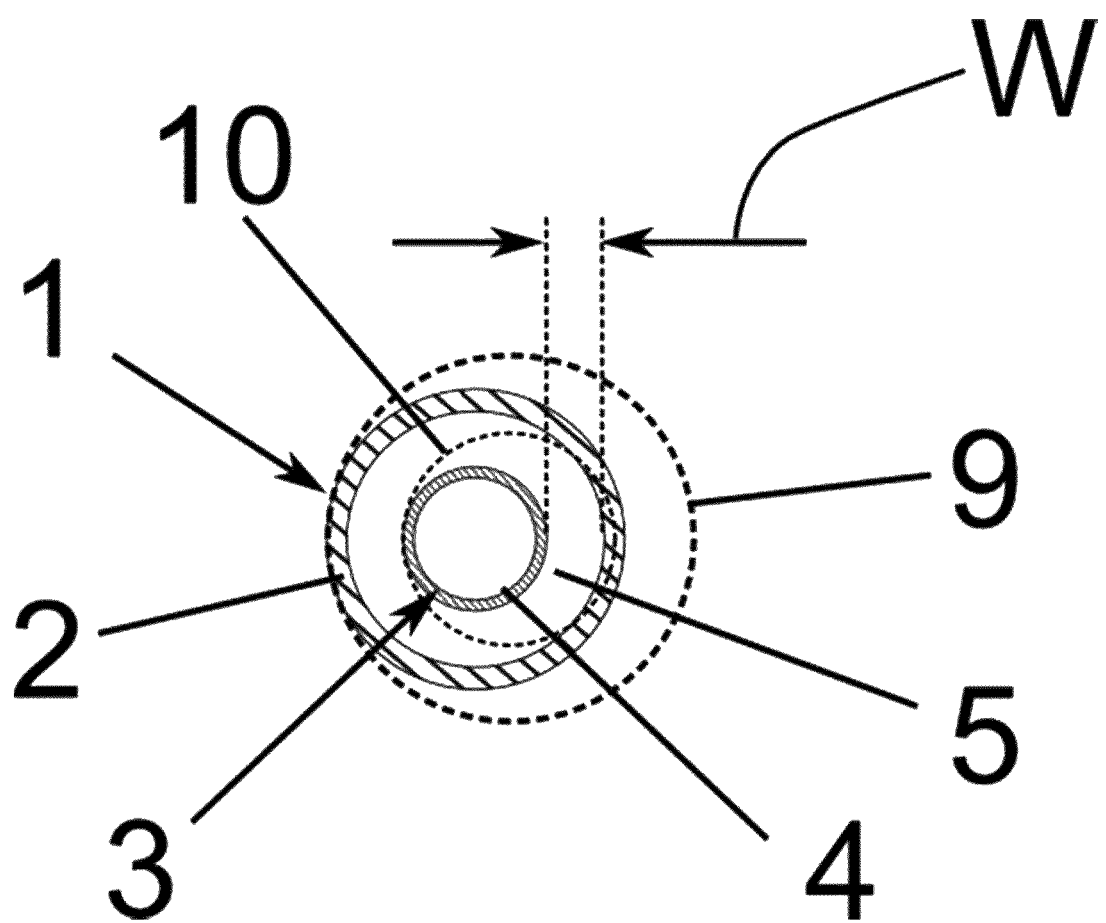
FIG. 2 is a transverse sectional view through the pyrolysis tube of FIG. 1 taken on lines II-II in FIG. 1.

Referring to FIGS. 1 and 2, a pyrolysis tube 1 comprises a radially outer tubular wall 2 which surrounds in a circumferentially extending manner an inner body 3. The inner body 3 is a hollow body and provides the pyrolysis tube with a radially inner wall 4, whereby the radially inner wall and the radially outer tubular wall together define an annular flow passage 5 for a flow F of fluid, which in this and the other illustrated and described embodiments, is a gas. The embodiments are applicable to cracking furnaces for producing ethylene, i.e. ethylene cracking furnaces.

The pyrolysis tube 1 has a central longitudinal axis 6, which is straight in this embodiment, and which may also be referred to as an axis of helical rotation. The central longitudinal axis 6 lies along the central axis of an imaginary cylindrical envelope 9 which contains the "footprint" of the pyrolysis tube when viewed in the longitudinal direction.

The radially outer tubular wall 2 has a centre line 7 which follows a helical path about the central longitudinal axis 6. The inner body 3 has a centre line 8 which follows a helical path about the central longitudinal axis 6. In this embodiment the helical centre line 7 of the radially outer tubular wall 2 and the helical centre line 8 of the inner body 3 are coincident, i.e. the centre lines are of the same pitch and amplitude and are in phase with each other. The flow passage 5 is a helically winding annular flow passage.

The inner body 3 is contained in an imaginary cylindrical envelope 10 which contains the "footprint" of the inner body when viewed in the longitudinal direction. The central longitudinal axis 6 lies along the central axis of the imaginary cylindrical envelope 10.

The helical centre line 7, 8 has an amplitude A and a pitch P. The inside diameter of the radially outer tubular wall 2 is shown as $D_O$ and the outside diameter of the inner body 3 is shown as $D_I$. In this specification the relative amplitude of a helical line is considered as the amplitude A of the helical line divided by the internal diameter $D_O$ of the radially outer tubular wall, i.e. $A/D_O$. The relative pitch is considered as the pitch P divided by the internal diameter $D_O$ of the radially outer tubular wall, i.e. $P/D_O$.

The annular flow passage 5 has a width W in the radial direction with respect to the central longitudinal axis 6. In this first type of pyrolysis tube the width W is constant around the annulus of the flow passage 5.

Figure 3:
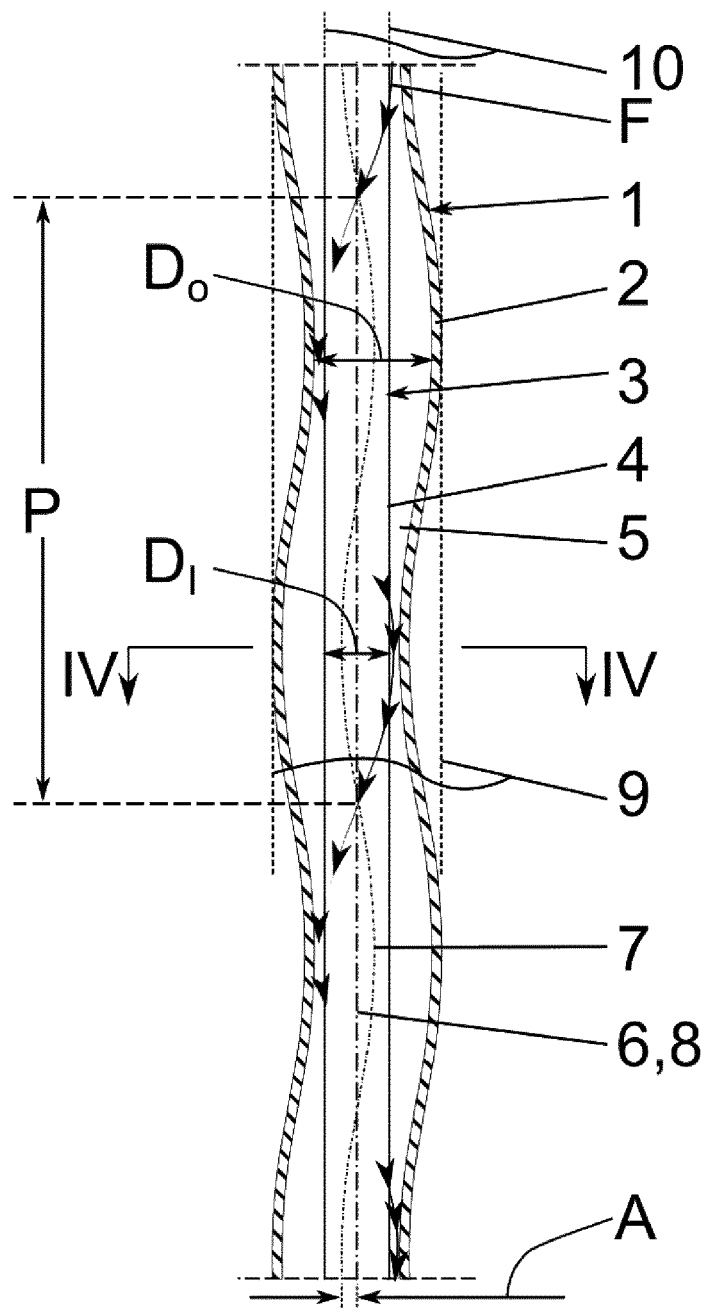
FIG. 3 is a schematic longitudinal sectional view of a portion of a second type of pyrolysis tube.
Figure 4:
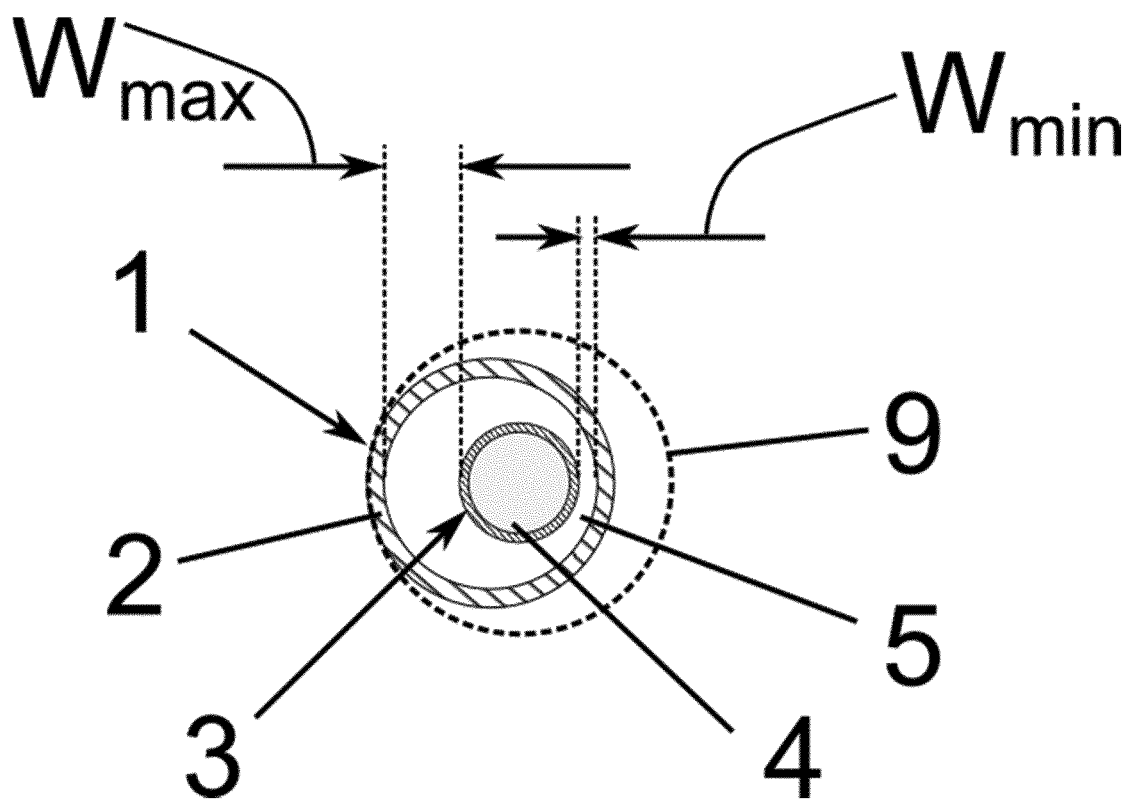
FIG. 4 is a transverse sectional view through the pyrolysis tube of FIG. 3 taken on lines IV-IV in FIG. 3.

FIGS. 3 and 4 show a second type of pyrolysis tube 1. Reference numerals corresponding to those used in FIGS. 1 and 2 are used where appropriate. The second type differs from the first type in that the inner body 3 is cylindrical rather than having a helical configuration. The inner body 3 is a hollow body and provides the pyrolysis tube with a radially inner wall 4, whereby the radially inner wall and the radially outer tubular wall together define an annular flow passage 5 for a flow F of gas.

The centre line 8 of the cylindrical inner body 3 lies on the central longitudinal axis 6 of the pyrolysis tube which lies along the central axis of an imaginary cylindrical envelope 9 containing the radially outer tubular wall 2 when viewed in the longitudinal direction. Thus, for this second type of pyrolysis tube, the inner body 3 has a straight centre line 8. In this case an imaginary cylindrical envelope 10 which contains the "footprint" of the inner body 3 when viewed in the longitudinal direction corresponds to the cylindrical shape of the inner body itself.

The radially outer tubular wall 2 has a centre line 7 which is helical, and this centre line has an amplitude A and a pitch P.

The effect is that the annular flow passage 5 has a helical configuration. As seen in FIG. 4, which shows the flow passage in a plane transverse to the longitudinal direction, the flow passage 5 has a minimum width $W_{min}$ in the transverse plane and a maximum width $W_{max}$ in the transverse plane. The positions of both the minimum width $W_{min}$ and the maximum width $W_{max}$, as viewed in the transverse plane, rotate along the length of the pyrolysis tube, i.e. with respect to the longitudinal direction. The flow passage 5 is thus a helically winding annular flow passage.

The inside diameter of the radially outer tubular wall 2 is shown as $D_O$ and the outside diameter of the inner body 3 is shown as $D_I$.

Figure 5:
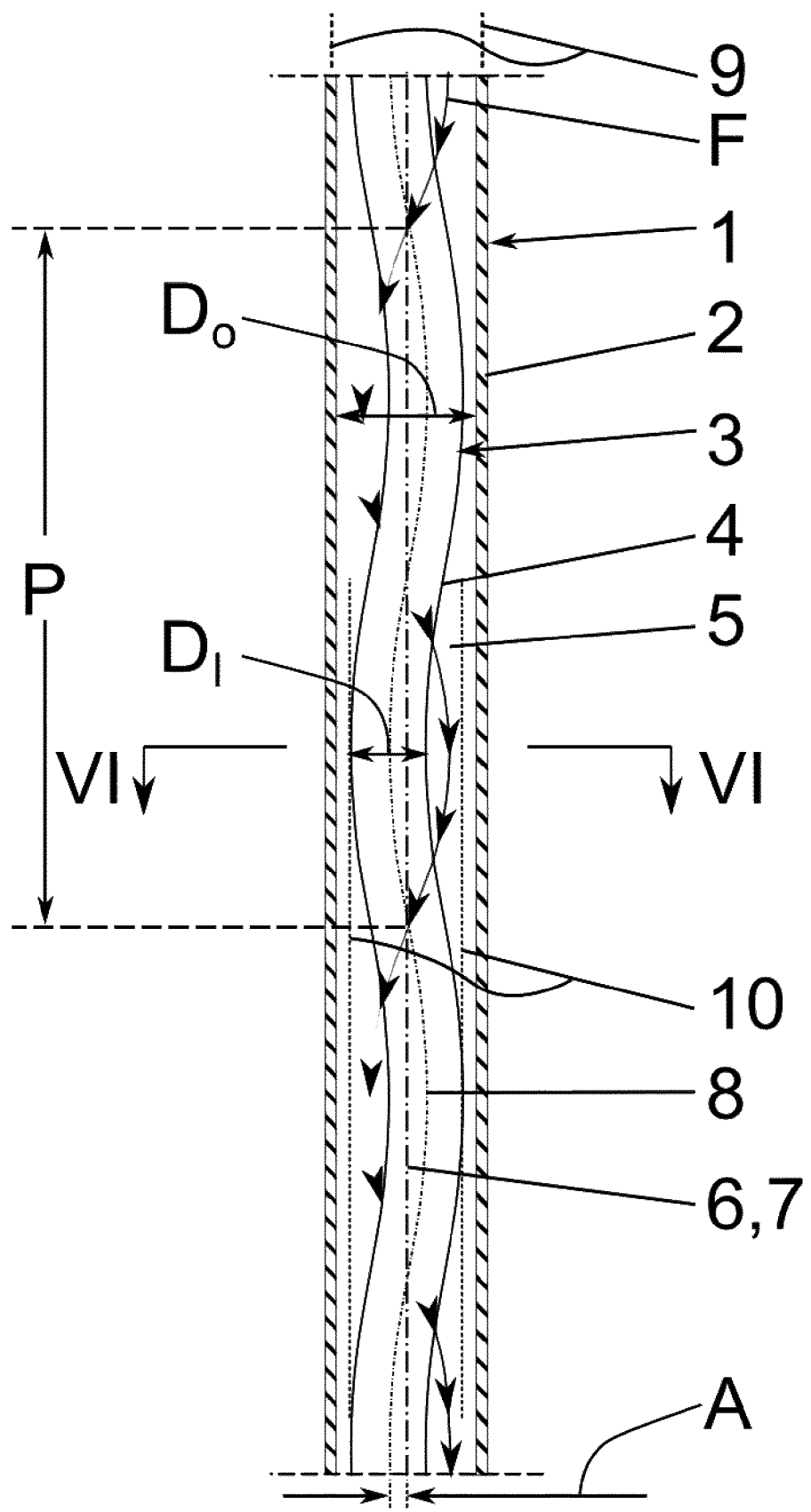
FIG. 5 is a schematic longitudinal sectional view of a portion of a third type of pyrolysis tube.
Figure 6:
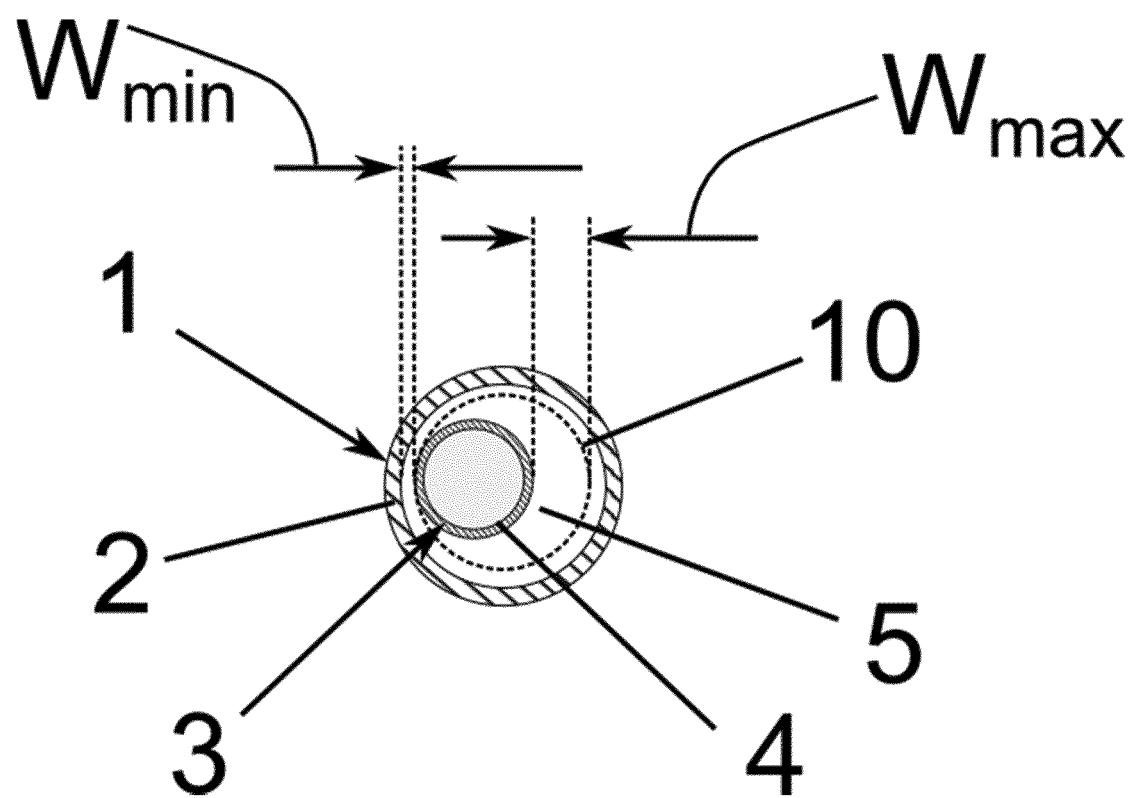
FIG. 6 is a transverse sectional view through the pyrolysis tube of FIG. 5 taken on lines VI-VI in FIG. 5.

FIGS. 5 and 6 show a third type of pyrolysis tube 1. Reference numerals corresponding to those used in FIGS. 1 and 2 are used in FIGS. 5 and 6 where appropriate. The third type differs from the first type in that the radially outer tubular wall 2 is cylindrical, rather than having a helical configuration. The inner body 3 is a hollow body and provides the pyrolysis tube with a radially inner wall 4, whereby the radially inner wall and the radially outer tubular wall together define an annular flow passage 5 for a flow F of gas.

The central longitudinal axis 6 of the pyrolysis tube for this third type is also the centre line 7 of the radially outer tubular wall 2 when viewed in the longitudinal direction. In this case an imaginary cylindrical envelope 9 which contains the "footprint" of the pyrolysis tube when viewed in the longitudinal direction corresponds to the cylindrical radially outer tubular wall 2.

The inner body 3 is helical and its centre line 8 follows a helical path about the central longitudinal axis 6 of the pyrolysis tube. The inner body 3 is contained in an imaginary cylindrical envelope 10 which contains the "footprint" of the inner body when viewed in the longitudinal direction. The central longitudinal axis 6 lies along the central axis of the imaginary cylindrical envelope 10.

The helical centre line 8 of the inner body 3 has a pitch P and an amplitude A.

Thus, for this third type of pyrolysis tube, the radially outer tubular wall 2 has a centre line 7 which is straight, whereas the inner body 3 has a centre line 8 which is helical. The effect is that the annular flow passage 5 has a helical configuration. As seen in FIG. 6, which shows the flow passage in a plane transverse to the longitudinal direction, the flow passage 5 has a minimum width $W_{min}$ in the transverse plane and a maximum width $W_{max}$ in the transverse plane. The positions of both the minimum width $W_{min}$ and the maximum width $W_{max}$, as viewed in the transverse plane, rotate along the length of the pyrolysis tube, i.e. with respect to the longitudinal direction. The flow passage 5 is thus a helically winding annular flow passage.

The inside diameter of the radially outer tubular wall 2 is shown as $D_O$ and the outside diameter of the inner body 3 is shown as $D_I$.

FIGS. 1 to 6 show the first, second and third types of pyrolysis tube. The radially outer wall 2 and/or the inner body 3 may be formed to have a helical centre line by extrusion. In that case, the radially outer wall 2 and/or the inner body 3 may be circular in a plane perpendicular to the axis of helical rotation, i.e. the central longitudinal axis 6. Alternatively, the radially outer wall 2 and/or the inner body 3 may be formed from a cylindrical tube or bar to have a helical centre line. In that case, the radially outer wall 2 and/or the inner body 3 may be circular in a plane perpendicular to the helical centre line 7 and/or 8.

Figure 7:
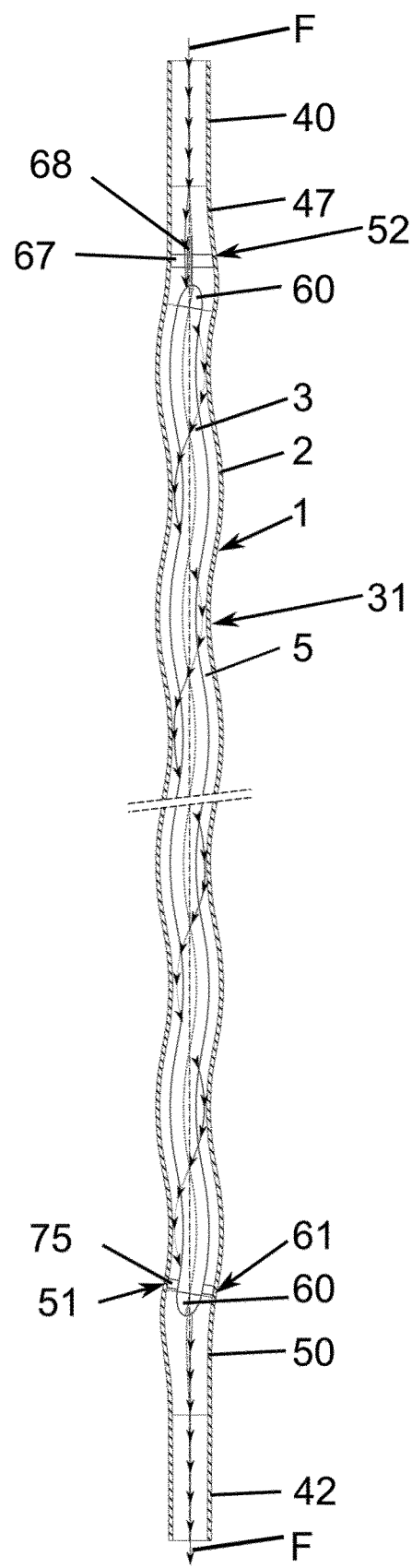
FIG. 7 is a schematic longitudinal sectional view of the first type of pyrolysis tube, showing its full length.

FIG. 7 shows the pyrolysis tube 1 of the first type in a form to be installed in a cracking furnace to provide a single pass through that furnace. The pyrolysis tube 1 has a main part in the form of an annular swirl flow section 31, which has a radially outer tubular wall 2 and an inner body 3. As the pyrolysis tube is of the first type, both the radially outer tubular wall 2 and the inner body 3 have a helical centre line. At an upper end the pyrolysis tube 1 has an inlet portion 40 and at a lower end it has an outlet portion 42. Both the inlet portion 40 and the outlet portion 42 are cylindrical and have respective straight centre lines. A first upper transitional portion 47 is located between the upper inlet portion 40 and the annular flow section 31, and a first lower transitional portion 50 is arranged between the annular flow section 31 and the outlet portion 42.

At its lower end the first upper transitional portion 47 joins to the radially outer tubular wall 2 of the annular swirl flow section 31 of the pyrolysis tube 1. It provides a transition from the upper inlet portion 40 with its straight central longitudinal axis to the radially outer tubular wall 2 with its helical centre line 7 (see FIG. 1).

The upper end of the first lower transitional portion 50 joins to the lower end of the radially outer tubular wall 2 of the annular swirl flow section 31. The first lower transitional portion 50 thus provides a transition from the radially outer tubular wall 2 with its helical centre line 7 to the outlet portion 42 with its straight centre line.

The inner body 3 has at its upper end an ogive 60 which is arranged to guide the flow F entering from the first upper transitional portion 47 to the annular flow passage 5 around the outside of the inner body 3 and the inside of the radially outer tubular wall 2. Both the radially outer tubular wall 2 and the inner body 3 have helical centre lines which are coincident.

The inner body 3 has at its lower end a second ogive 60 which is arranged to guide the flow F as it leaves the annular flow passage.

A first support arrangement 51 is provided for holding the inner body 3 at a lower end thereof in the radially outer tubular wall 2. A similar support arrangement 51 is provided for the pyrolysis tube of the second type shown in FIG. 8, with further details being seen in FIGS. 9 and 10. A support 61 is provided at the lower region of the inner body 3 and consists of three equiangularly spaced radial support members 75, which extend in a radial direction between the radially outer tubular wall 2 and the inner body 3. The radial support members 75 have a low profile in the longitudinal direction so as to minimise the disruption to the flow F through the pyrolysis tube 1. The radial support members 75 of the support 61 hold the inner body 3 in a central position with respect to the radially outer tubular wall 2. The support 61 bears the weight of the inner body 3.

Referring back to FIG. 7, at an upper end of the inner body 3 a second support arrangement 52 is provided for holding the inner body 3 centrally in the radially outer tubular wall 2. The second support arrangement includes a guide pin 68 which projects upwardly into a space defined radially inwardly of a spacer ring (not shown). The spacer ring is supported by three equiangularly spaced radial support members 67 which project radially inwardly from the radially outer tubular wall 2 to the spacer ring and thereby hold it in position. The guide pin 68 is loosely retained by the spacer ring so that it remains in a generally central position inside the radially outer tubular wall 2. Relative thermal expansion of the radially outer tubular wall 2 and the inner body 3 is permitted by virtue of the loose support provided by the spacer ring to the guide pin 68 at the top of the inner body 3.

Figure 8:
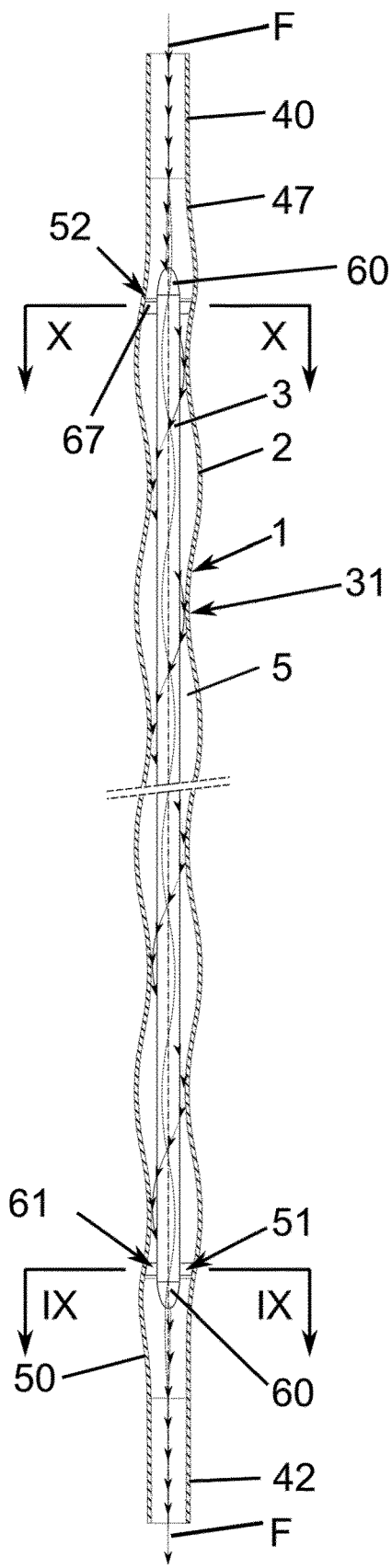
FIG. 8 is a schematic longitudinal sectional view of the second type of pyrolysis tube, showing its full length.

FIG. 8 shows a pyrolysis tube 1 based on the second type (as shown in FIGS. 3 and 4) for use as a single pass pyrolysis tube in a cracking furnace. The illustrated pyrolysis tube 1 has a main part in the form of an annular swirl flow section 31, which has a radially outer tubular wall 2 with a helical centre line, and an inner body 3 with a centre line which is straight.

A first upper transitional portion 47 is located between the upper inlet portion 40 and the annular flow section 31, and a first lower transitional portion 50 is arranged between the annular flow section 31 and the outlet portion 42.

At its lower end the first upper transitional portion 47 joins to the radially outer tubular wall 2 of the annular swirl flow section 31 of the pyrolysis tube 1. It provides a transition from the upper inlet portion 40 with its straight central longitudinal axis to the radially outer tubular wall 2 with its helical centre line 7 (see FIG. 3).

The upper end of the first lower transitional portion 50 joins to the lower end of the radially outer tubular wall 2 of the annular swirl flow section 31. The first lower transitional portion 50 thus provides a transition from the radially outer tubular wall 2 with its helical centre line 7 to the outlet portion 42 with its straight centre line.

The inner body 3 has at its upper end an ogive 60 which is arranged to guide the flow F entering from the first upper transitional portion 47 to the annular flow passage 5 around the outside of the inner body 3 and the inside of the radially outer tubular wall 2.

The inner body 3 has at its lower end a second ogive 60 which is arranged to guide the flow F as it leaves the annular flow passage.

Figure 9:
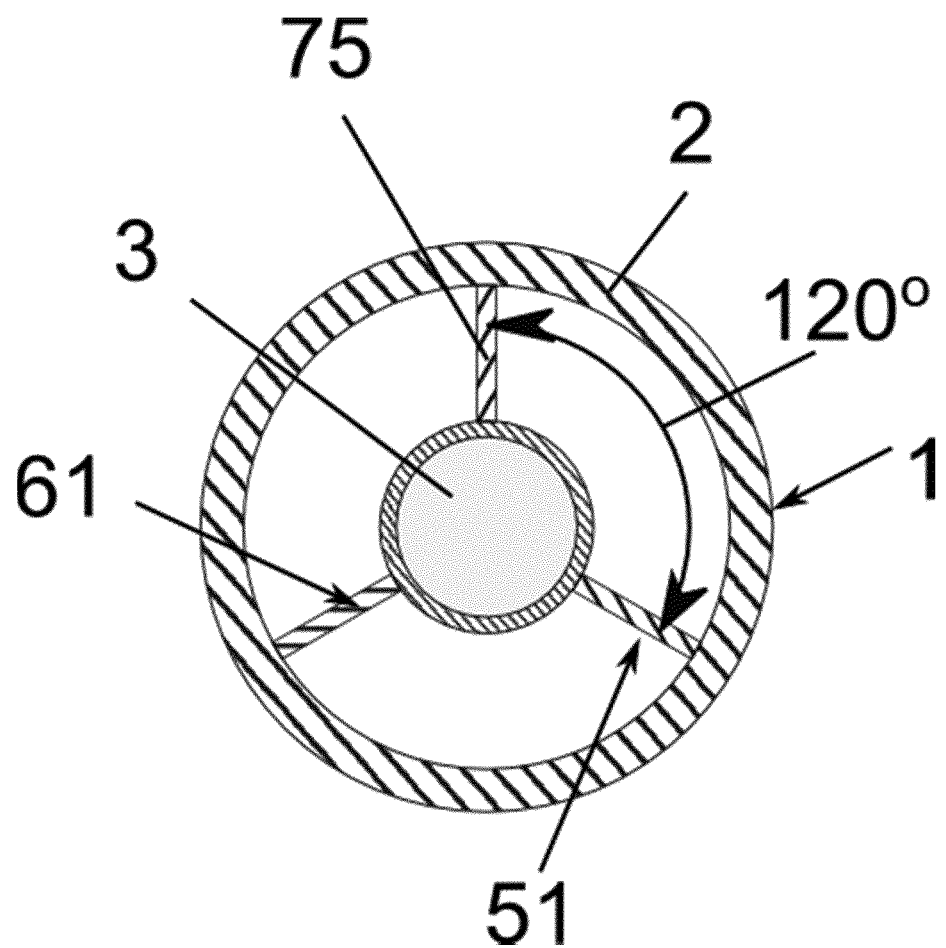
FIG. 9 is a transverse sectional view taken on lines IX-IX in FIG. 8.

The inner body 3, although in this case having a straight centre line rather than a helical one, is supported at its lower end in a similar manner as described in relation to FIG. 7. Further details are shown in FIG. 9. Thus a support arrangement 51 has a support 61 provided in a lower region of the inner body 3.

The support 61 consists of three equiangularly spaced radial support members 75 which extend in a radial direction between the radially outer tubular wall 2 and the inner body 3. As can be seen in FIG. 9, the radial support members 75 have a low profile in the longitudinal direction so as to minimise the disruption to the flow F through the pyrolysis tube 1. The radial support members 75 of the support 61 hold the inner body 3 in a central position with respect to the radially outer tubular wall 2. The support 61 bears the weight of the inner body 3. The angle 120° between circumferentially adjacent radial support members 75 is shown in FIG. 9.

Figure 10:
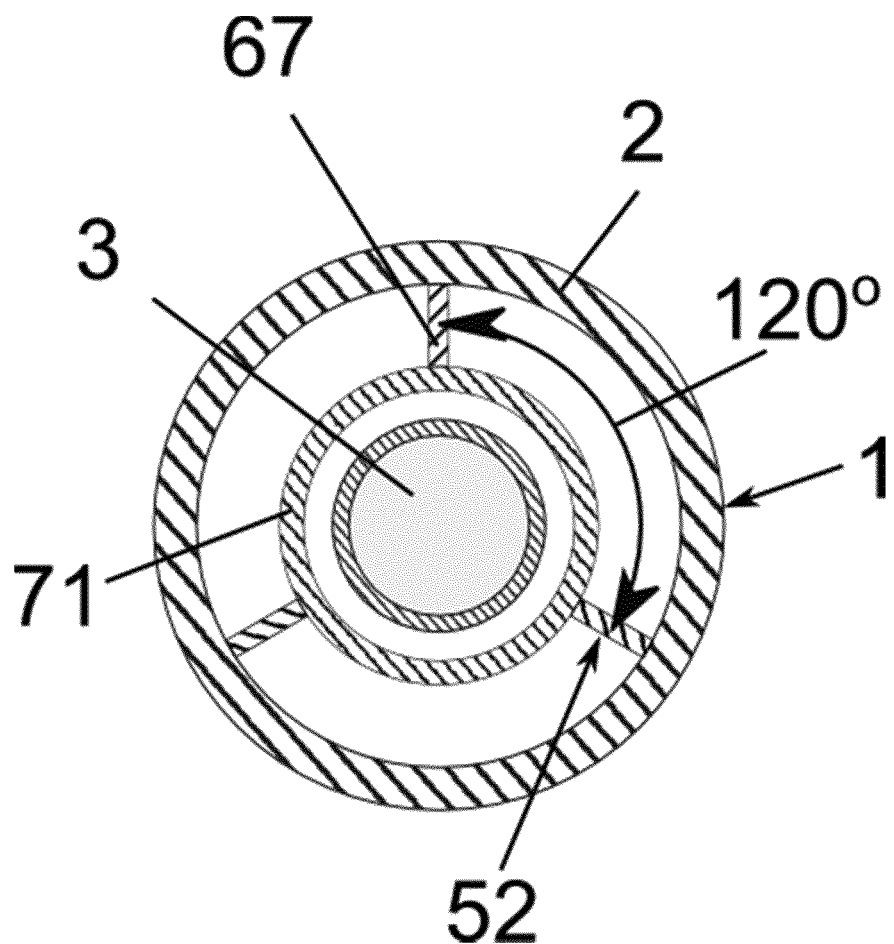
FIG. 10 is a transverse sectional view taken on lines X-X in FIG. 8.

At an upper end of the inner body 3 a second support arrangement 52 is provided for holding the inner body 3 centrally in the radially outer tubular wall 2. The second support arrangement 52 includes a spacer ring 71 which defines a space radially inwardly thereof in which the inner body 3 extends. The spacer ring 71 is supported by 3 equiangularly spaced radial support members 67 which project radially inwardly from the radially outer tubular wall 2 to the spacer ring 71 and thereby hold it in position. The angle 120° between circumferentially adjacent radial support members 67 is shown in FIG. 10.

The inner body 3 is loosely retained by the spacer ring 71 and the top of the inner body so that it remains in a generally central position inside the radially outer tubular wall 2. Relative thermal expansion of the radially outer tubular wall 2 and the inner body 3 is permitted by virtue of the loose support provided by the spacer ring 71 to the inner body 3 at the top thereof.

Figure 11:
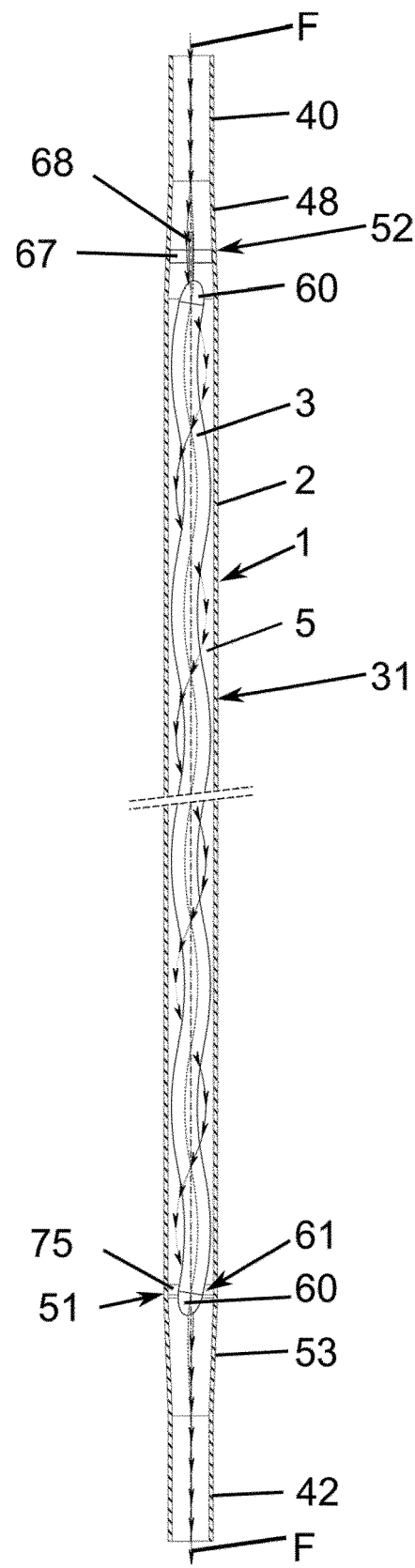
FIG. 11 is a schematic longitudinal sectional view of the third type of pyrolysis tube, showing its full length.

FIG. 11 shows a pyrolysis tube 1 based on the third type (as shown in FIGS. 5 and 6) for use as a single pass pyrolysis tube in a cracking furnace. The illustrated pyrolysis tube 1 has a main part in the form of an annular swirl flow section 31, which has a radially outer tubular wall 2 with a straight centre line, and an inner body 3 with a helical centre line.

A second upper transitional portion 48 is located between the upper inlet portion 40 and the annular flow section 31, and a second lower transitional portion 53 is arranged between the annular flow section 31 and the outlet portion 42.

At its lower end the second upper transitional portion 48 joins to the radially outer tubular wall 2 of the annular swirl flow section 31 of the pyrolysis tube 1. It is conical in shape and provides a transition from the upper inlet portion 40 which has a straight central longitudinal axis and a smaller diameter than that of the radially outer tubular wall 2 with its straight centre line 7 (see FIG. 5).

The upper end of the second lower transitional portion 53 joins to the lower end of the radially outer tubular wall 2 of the annular swirl flow section 31. The second lower transitional portion 53 is conical in shape and provides a transition from the radially outer tubular wall 2 which has a straight centre line 7 and a larger diameter than that of the outlet portion 42 with its straight central longitudinal axis.

The inner body 3 has at its upper end an ogive 60 which is arranged to guide the flow F entering from the second upper transitional portion 48 to the annular flow passage 5 around the outside of the inner body 3 and the inside of the radially outer tubular wall 2.

The inner body 3 has at its lower end a second ogive 60 which is arranged to guide the flow F as it leaves the annular flow passage.

The inner body 3 is supported at its lower end by a first support arrangement 51 which is the same as that described in relation to FIG. 7. The upper end of the inner body 3 is supported by a second support arrangement 52 which is the same as that described in relation to FIG. 7.

Figure 12:
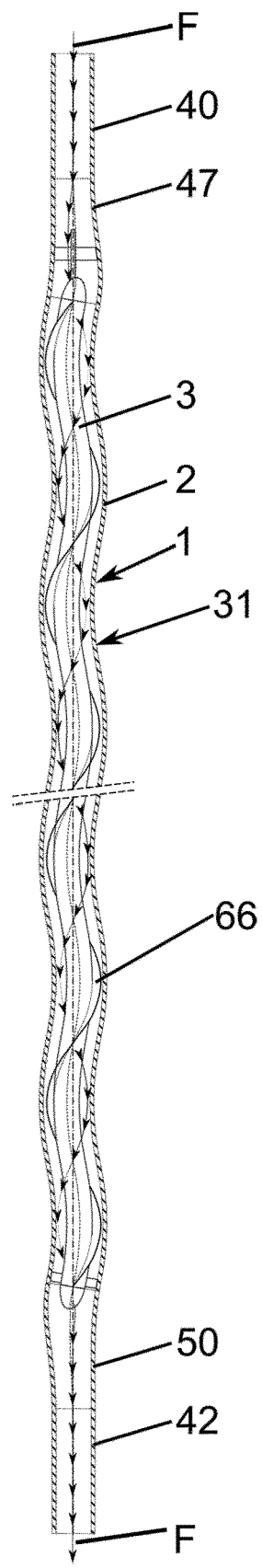
FIG. 12 is a schematic longitudinal sectional view of the first type of pyrolysis tube, showing its full length, and modified to include a fin.

FIG. 12 shows a pyrolysis tube 1 based on the first type (as shown in FIGS. 1 and 2) for use as a single pass pyrolysis tube in a cracking furnace. In this case, the inner body is provided with a helically curved longitudinal fin 66. The helical fin 66 has a helical configuration with the same handedness as the helical configuration of the inner body 3. The phases of the helical fin 66, of the inner body 3 and of the radially outer tubular wall 2 are in phase.

Figure 13:
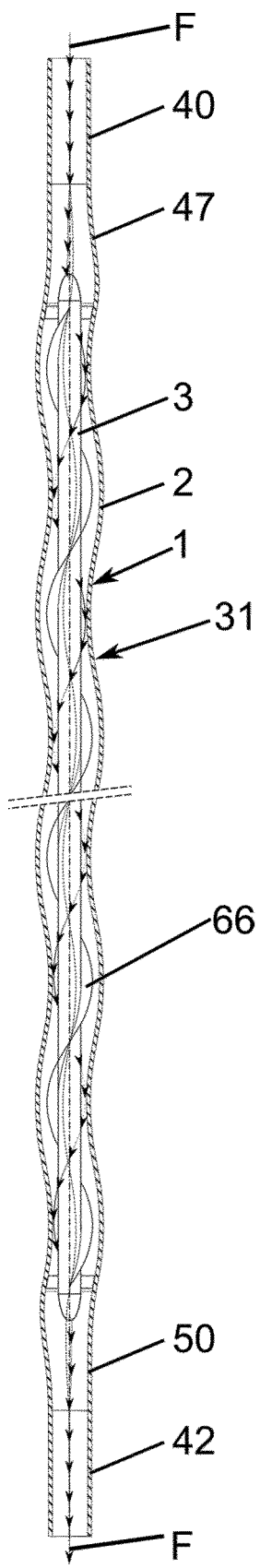
FIG. 13 is a schematic longitudinal sectional view of the second type of pyrolysis tube, showing its full length, and modified to include a fin.

FIG. 13 shows a pyrolysis tube 1 based on the second type (as shown in FIGS. 3 and 4) for use as a single pass pyrolysis tube in a cracking furnace. In this case, the cylindrical inner body 3 is provided with a helically curved longitudinal fin 66. The helical fin 66 has a helical configuration with the same handedness as the helical configuration of the radially outer tubular wall 2. The phases of the helical fin 66 and of the radially outer tubular wall 2 are in phase.

Figure 14:
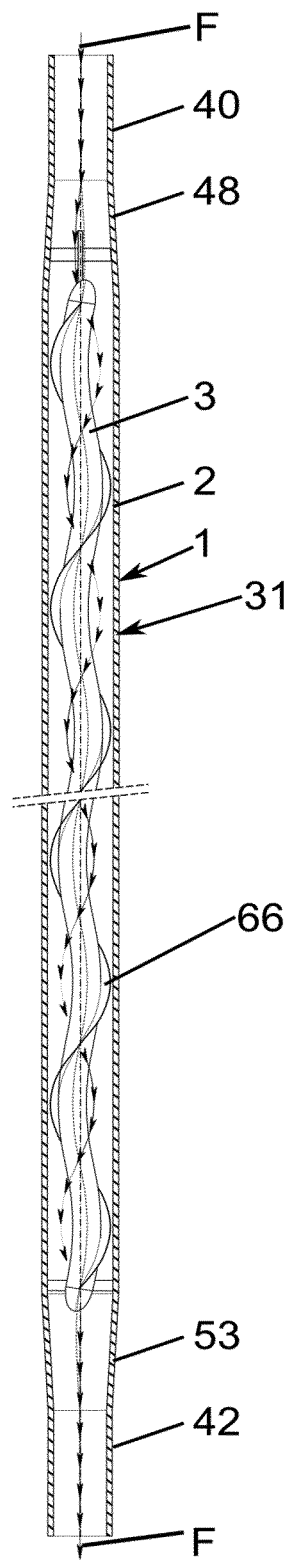
FIG. 14 is a schematic longitudinal sectional view of the third type of pyrolysis tube, showing its full length, and modified to include a fin.

FIG. 14 shows a pyrolysis tube 1 based on the third type (as shown in FIGS. 5 and 6) for use as a single pass pyrolysis tube in a cracking furnace. In this case, the inner body is provided with a helically curved longitudinal fin 66. The helical fin 66 has a helical configuration with the same handedness as the helical configuration of the inner body 3. The helical fin 66 has a helical configuration in phase with that of the inner body 3.

Figure 15:
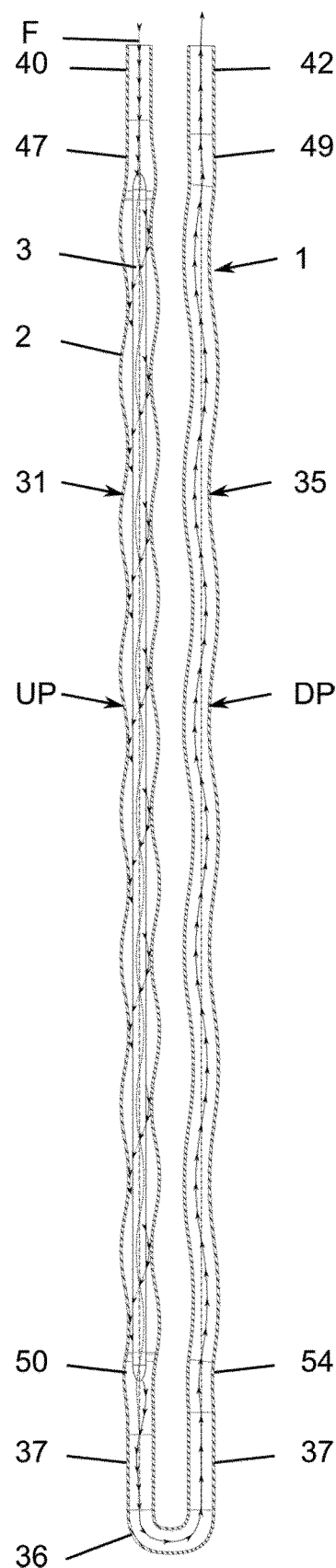
FIG. 15 is a schematic longitudinal sectional view of the second type of pyrolysis tube, for use in a dual pass arrangement whereby the pyrolysis tube passes twice through the length of a cracking furnace.

FIG. 15 shows a pyrolysis tube 1 based on the second type (as shown in FIGS. 3 and 4), for use in a dual pass arrangement whereby the pyrolysis tube passes twice through the length of a cracking furnace. The pyrolysis tube is generally U-shaped and has an annular swirl flow section 31 in an upstream portion UP thereof, i.e. the upstream limb of the "U", and a swirl flow section 35 in a downstream portion DP thereof, i.e. the downstream limb of the "U".

As with all the other swirl flow sections 35 disclosed herein, the swirl flow section 31 has no inner body and so the passage defined therein is non-annular. The passage has a generally circular cross-sectional shape.

A flow F of gas enters via a straight inlet portion 40 and exits via a straight outlet portion 42. A first upper transitional portion 47 is arranged below the inlet portion 40, between the inlet portion 40 and the annular swirl flow section 31. A third upper transitional portion 49 is arranged below the outlet portion 42, between the swirl flow section 35 and the outlet portion 42. The third upper transitional portion 49 provides a transition between the swirl flow section 35 with its helical centre line and the outlet portion 42 with its straight central longitudinal axis.

A first lower transitional portion 50 is arranged below the annular swirl flow section 31, between that annular swirl flow section and a first straight intermediate section 37. A third lower transitional portion 54 is arranged above a second straight intermediate section 37, between that section 37 and the swirl flow section 35. The third lower transitional portion 54 provides a transition between the second straight intermediate section 37 with its straight longitudinal central axis and the swirl flow section 35 with its helical centre line. A U-bend section 36 is arranged to connect the first and second straight intermediate sections 37.

The annular swirl flow section 31 includes an inner body 3 supported by a first support arrangement 51 at the lower end thereof, and by a second support arrangement 52 at the upper end thereof. The configuration of the inner body 3, the radially outer tube 2 in which it is supported and its support arrangements 51 and 52 are the same as those described in relation to FIGS. 8, 9 and 10.

Figure 16:
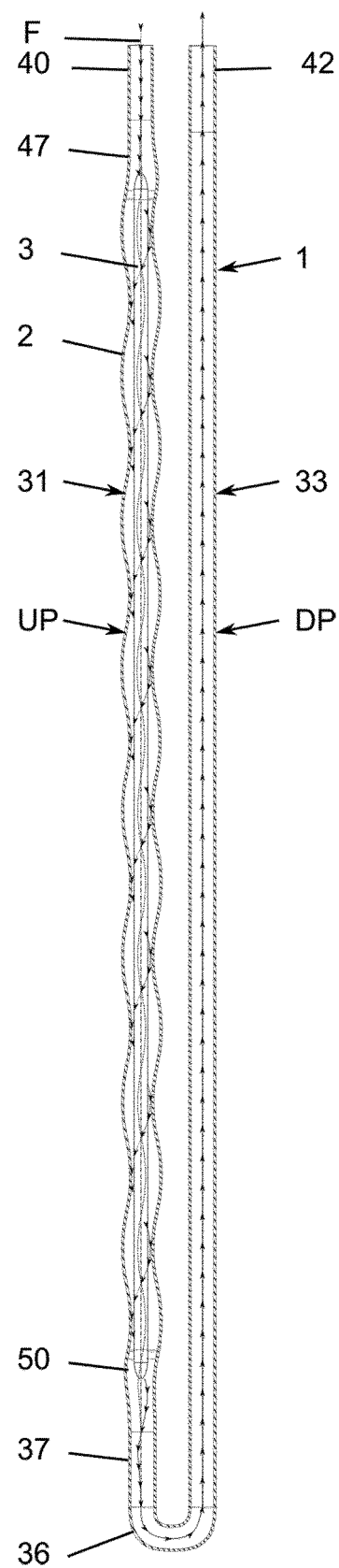
FIG. 16 is a schematic longitudinal sectional view of a variation of the second type of pyrolysis tube, for use in a dual pass arrangement whereby the pyrolysis tube passes twice through the length of a cracking furnace.

FIG. 16 shows a pyrolysis tube 1 similar to that of FIG. 15, except that instead of a swirl flow section 35 being provided downstream of the U-bend section 36, there is conventional flow section 33. This connects directly to the U-bend section 36 at its lower end and directly to the outlet portion 42 at its upper end.

Figure 17:
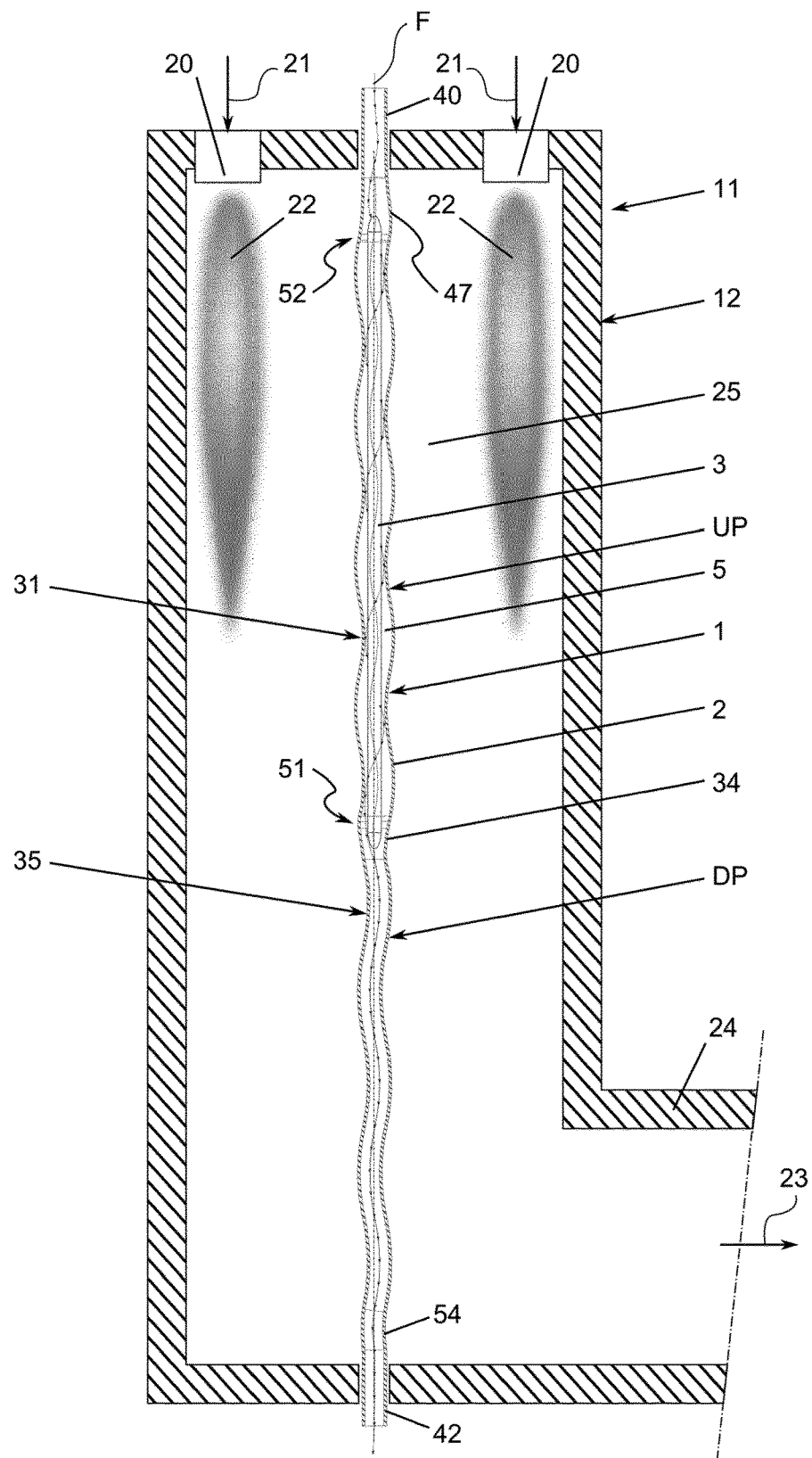
FIGS. 17-23 are schematic sectional views in a vertical plane of cracking furnaces having pyrolysis tubes.

FIG. 17 shows a cracking furnace 11 having a top fired fire box 12 through which passes a pyrolysis tube 1. A pair of downfiring burners 20 is provided in a roof of the fire box 12. The burners are arranged to receive a fuel/air mixture 21, whereby burner flames 22 are directed downwardly into the fire box 12. The fire box 12 has an L-shape and includes a flue gas outlet portion 24 through which, in use, flue gas 23 is exhausted from the fire box.

A pyrolysis tube 1 is arranged to provide a single pass through the fire box 12. The pyrolysis tube has an upstream portion UP with an annular swirl flow section 31 and a downstream portion DP with a swirl flow section 35.

A straight inlet portion 40 is arranged to receive a flow F of gas. The inlet portion 40 is connected to a first upper transitional portion 47 which is connected to the annular swirl flow section 31 in a combustion zone 25 of the fire box. An intermediate transitional portion 34 is provided below the annular swirl flow section 31, between that annular swirl flow section and the swirl flow section 35. A third lower transitional portion 54 is provided below the swirl flow section 35, between that swirl flow section and an outlet portion 42.

The annular swirl flow section 31 has a configuration corresponding to the second type of pyrolysis tube, described in relation to FIGS. 3 and 4. It has a cylindrical inner body 3, a helical radially outer tubular wall 2 and an annular flow passage 5 which is a helically winding annular flow passage. The further constructional details of the annular swirl flow section 31, including the first support arrangement 51 at the lower end of the inner body 3 and the second support arrangement 52 at the upper end of the inner body, correspond to those described in FIGS. 8, 9 and 10.

The arrangement of FIG. 17 provides for a helically winding annular flow passage upstream of a helical flow passage.

Figure 18:
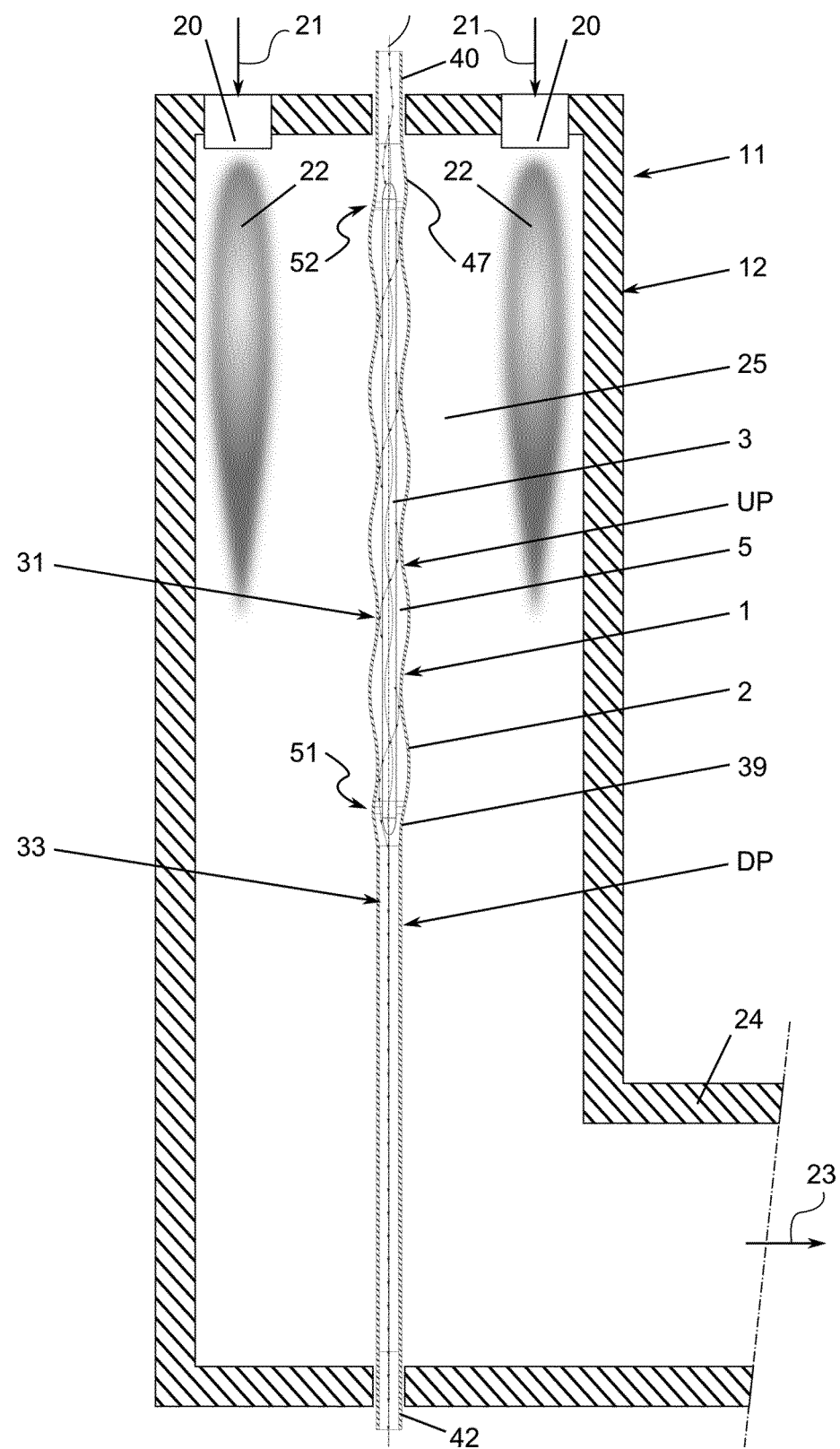

FIG. 18 shows another embodiment of cracking furnace similar to that of FIG. 17 and therefore using the same reference numerals to indicate the same features. The embodiment of FIG. 18 comprises a cracking furnace 11 with a top fired furnace chamber or firebox 12 and a pyrolysis tube 1 extending in a single pass arrangement for a flow F of gas. The upstream portion UP of the pyrolysis tube 1 is constructed in accordance with the second type of pyrolysis tube, having an annular swirl flow section 31 with a cylindrical inner body 3 and a helical radially outer tubular wall 2, in the same manner as the embodiment of FIG. 17. However, downstream of the upstream portion UP the downstream portion DP comprises a conventional flow section 33, i.e. one having a cylindrical radially outer tubular wall with a straight centre line, rather than the swirl flow section 35 as shown in FIG. 17. The annular swirl flow section 31 is connected via a second intermediate transitional portion 39 to the conventional flow section 33, providing a transition from helical to straight.

Thus in the embodiment of FIG. 18, the pyrolysis tube 1 has an upstream portion UP with a flow passage 5 which is a helically winding annular flow passage, and a downstream portion DP which is a conventional cylindrical flow section, having a cylindrical radially outer tubular wall and no inner body.

Figure 19:
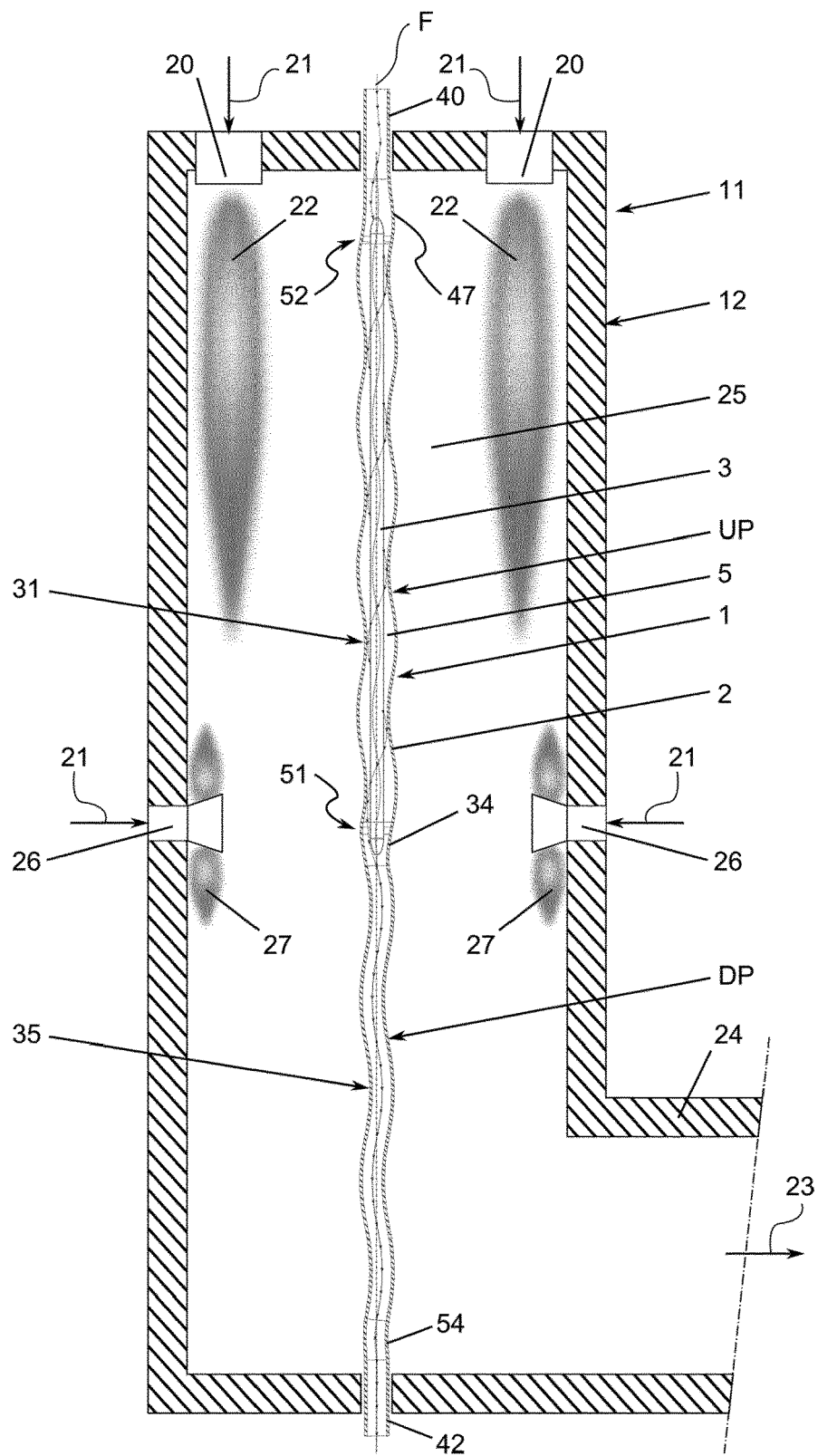

FIG. 19 shows another embodiment of cracking furnace 11 having a fire box 12 and a single pass pyrolysis tube 1 for a flow F of gas from top to bottom. The pyrolysis tube 1 has the same configuration as that of FIG. 17 and so the description of that Figure is applicable to the FIG. 19 embodiment. The firebox of FIG. 19 has down firing burners 20 which are also the same as those of FIG. 17 and so the description thereof is also applicable here. The difference between the embodiment of FIG. 19 and that of FIG. 17 is that the firebox 12 is provided with a pair of side wall burners 26 each for receiving an input of fuel/air mixture 21 for producing flames 27.

Figure 20:
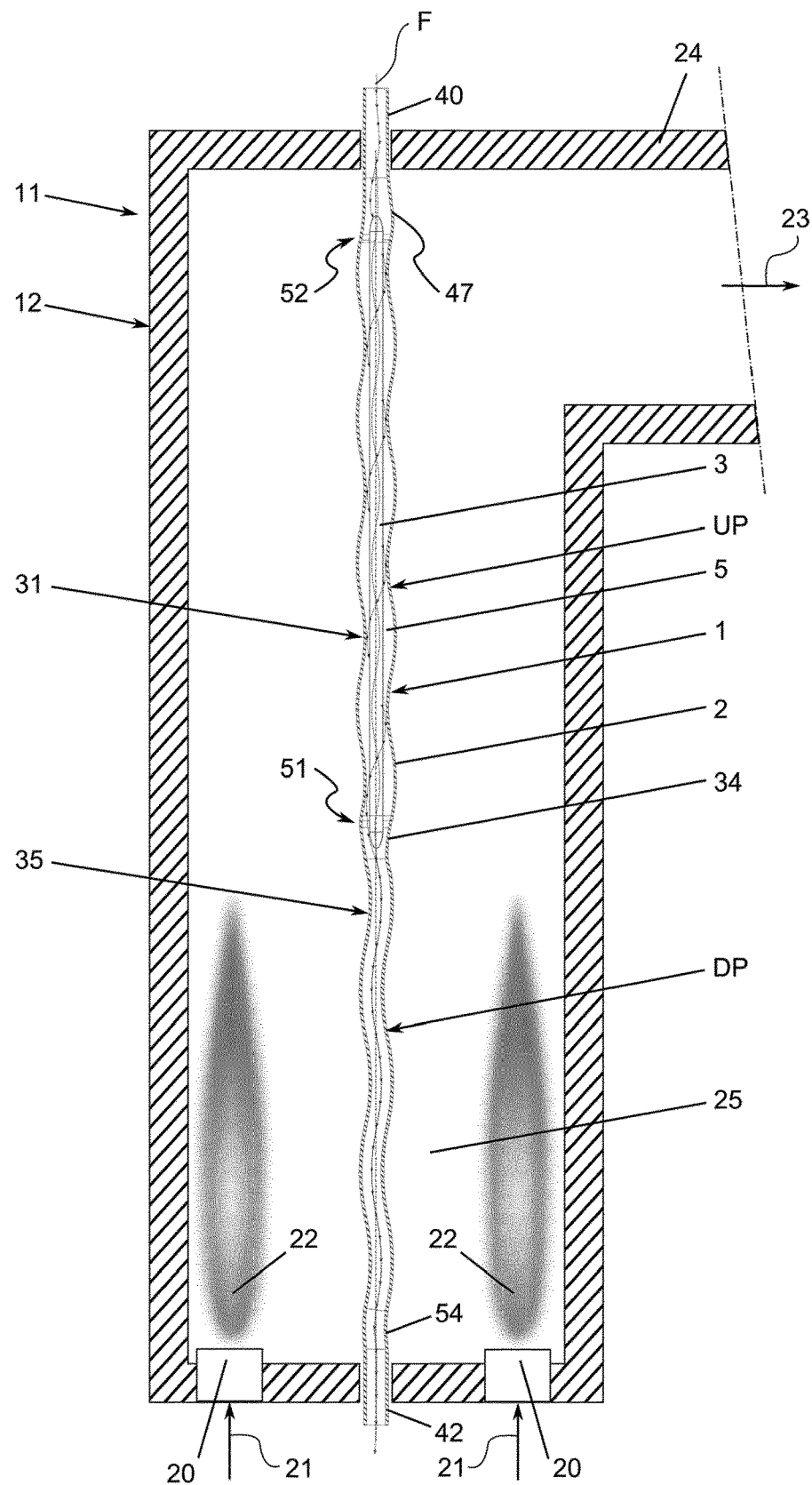

FIG. 20 shows another embodiment of cracking furnace 11, in this case having a bottom fired firebox 12. A pair of up firing burners 20 is provided in the floor of the firebox 12 for receiving respective flows of fuel/air mixture 21. The firebox 12 is shaped in the form of an upside down "L" and has a flue gas outlet 24 for the exhaust of flue gas 23.

The cracking furnace of FIG. 20 is provided with a pyrolysis tube 1 having the same configuration as that of FIG. 17. A flow F of gas passes through the pyrolysis tube 1 in a single pass from top to bottom. The description of the pyrolysis tube 1 in relation to FIG. 17 is also applicable to the pyrolysis tube 1 of FIG. 20.

In the case of the embodiment of FIG. 20, the combustion zone 25 is in a lower part of the firebox 12. Therefore, in use, the flow F of gas flows from a flow passage 5 which is a helically winding annular flow passage situated in a non-combustion zone of the firebox, into the swirl flow section 35 (which is not annular) in the combustion zone 25 of the firebox.

Figure 21:
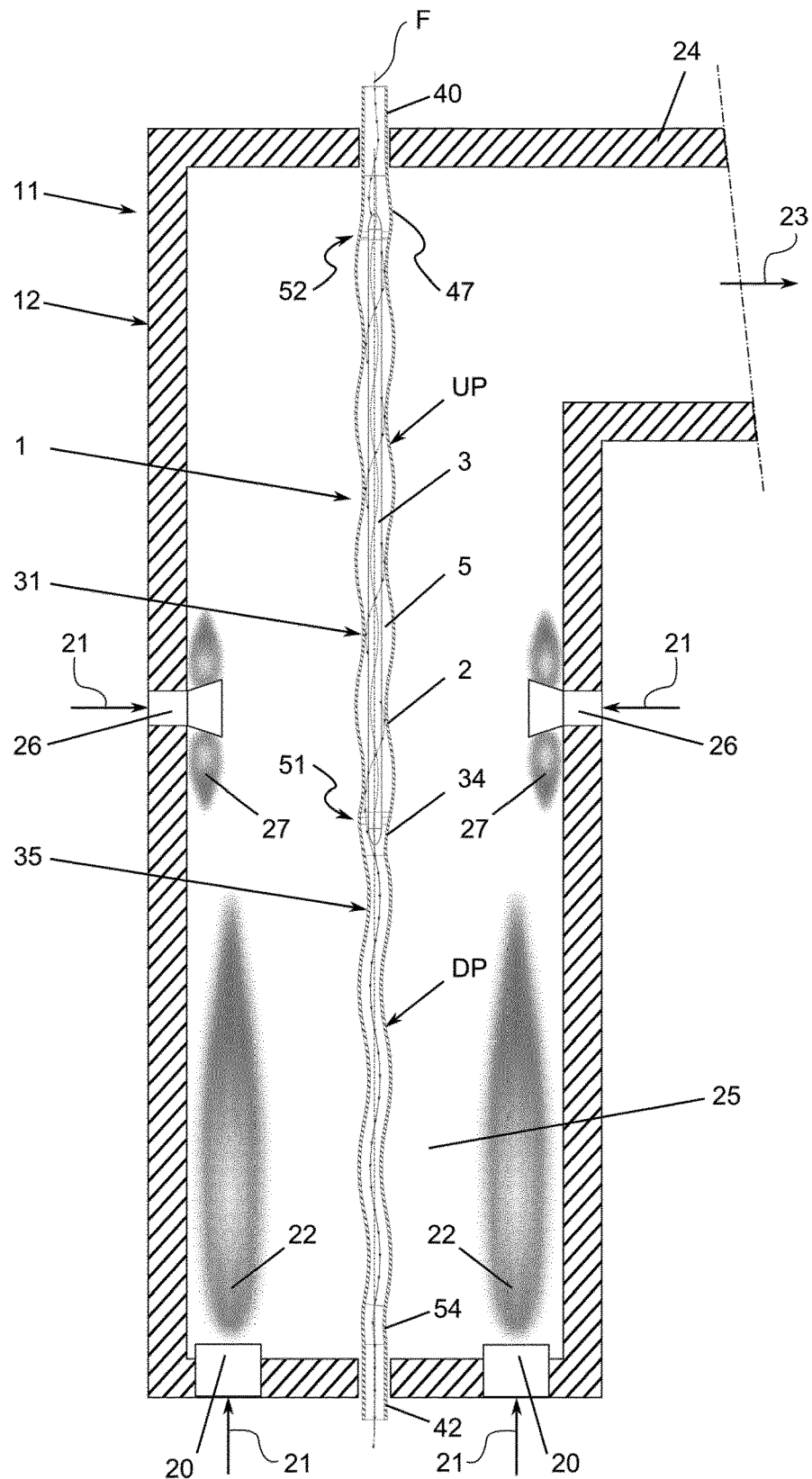

FIG. 21 shows another embodiment of cracking furnace 11 having a firebox 12 and a pyrolysis tube 1. The features of this embodiment are the same as those of the FIG. 20 embodiment and so the description of the FIG. 20 embodiment is applicable to the FIG. 21 embodiment. The FIG. 21 embodiment differs from that of FIG. 20 by the additional provision of side wall burners 26 into which a fuel/air mixture 21 is fed to produce flames 27.

Figure 22:
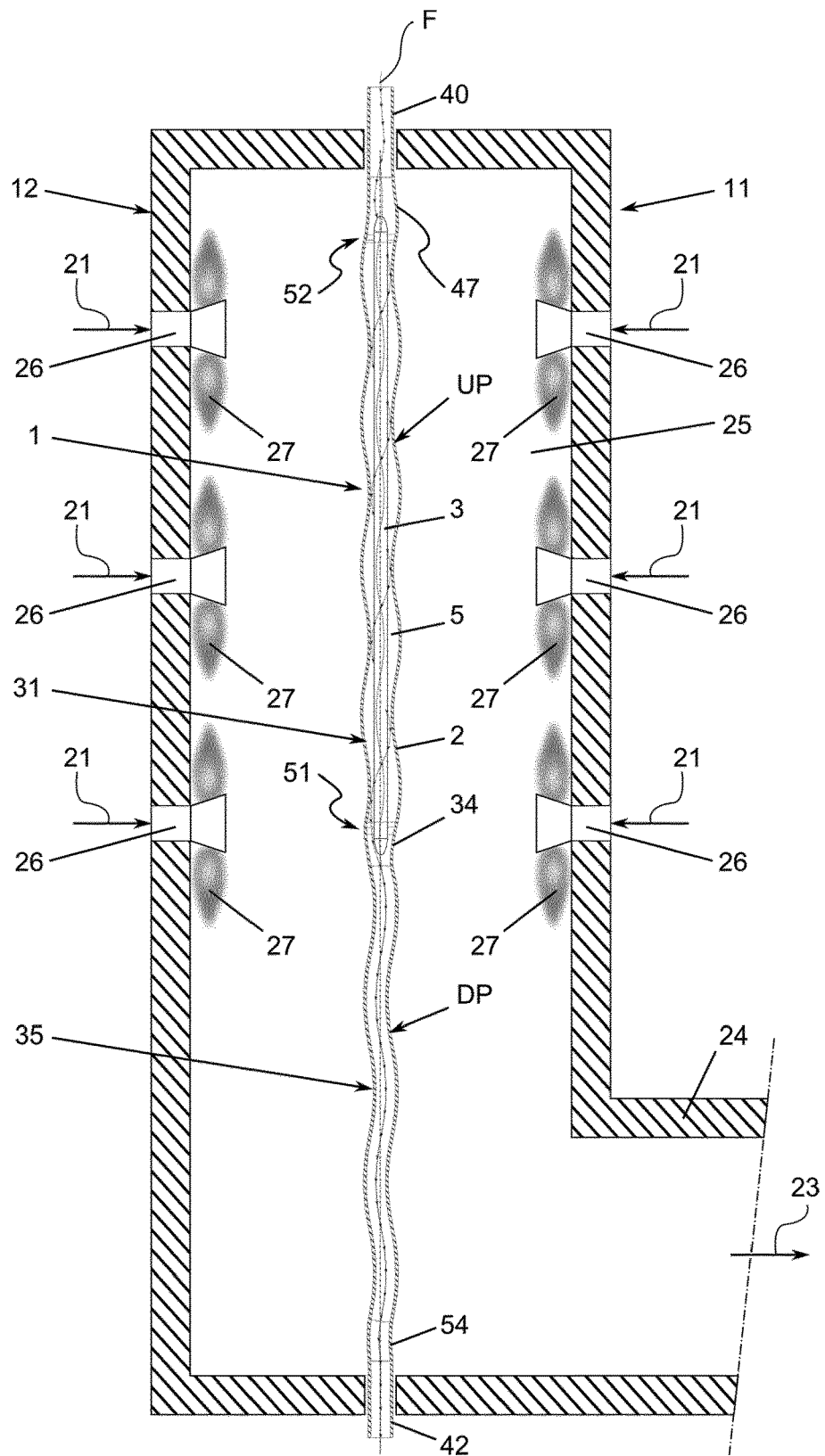

FIG. 22 shows another embodiment of cracking furnace 11 having a firebox 12 and a pyrolysis tube 1 extending therethrough in a single pass. The construction of the pyrolysis tube 1 is the same as that of FIG. 17 and so the description of FIG. 17 is also applicable to the embodiment of FIG. 22. The embodiment of FIG. 22 differs from that of FIG. 17 in that the cracking furnace has a side-fired firebox. A plurality of side wall burners 26 is provided in the side walls of the firebox 12, each receiving an input of fuel/air mixture 21 to produce a combustion flame 27. The side wall burners are arranged at three levels, an upper level near the roof of the firebox 12 and then two respective levels below the upper level. The combustion zone of the firebox 12 is thus generally in the upper half of the firebox and the annular swirl flow section 31 of the pyrolysis tube 1 passes through this combustion zone. The swirl flow section 35, which does not have an annular flow passage, is provided downstream of the combustion zone 25.

Figure 23:
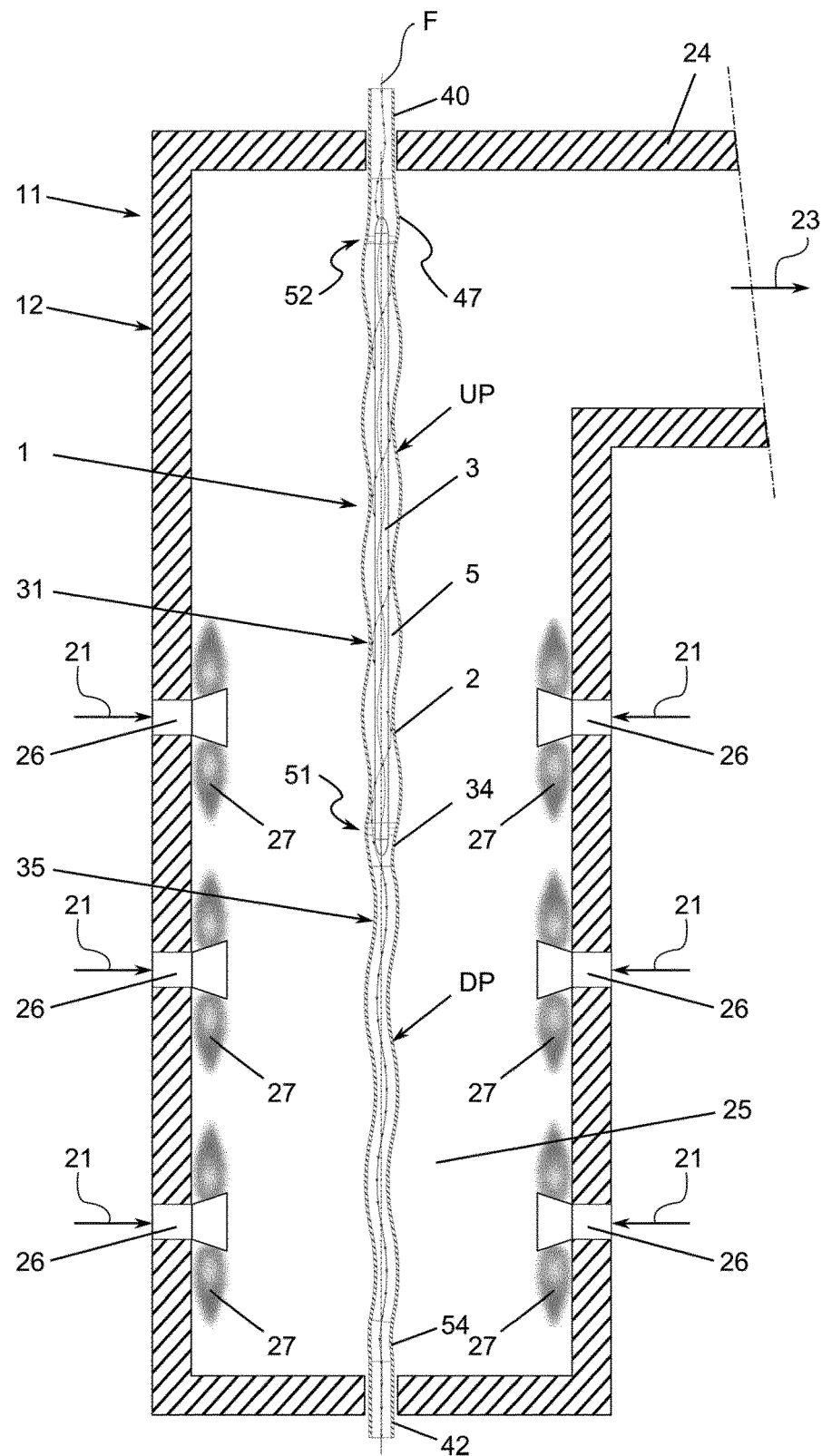

FIG. 23 shows another embodiment of cracking furnace 11 with a firebox 12 and a pyrolysis tube 1. The construction of the pyrolysis tube 1 is the same as that of FIG. 20 and so the description of that Figure is also applicable to FIG. 23. In the FIG. 23 embodiment the flue gas outlet 24 for the exhausting of the flue gas 23 is the same as that of FIG. 20, but the burner arrangement is different. In FIG. 23, the firebox 12 has a plurality of side mounted burners 26 which receive fuel/air mixture flows 21 to produce flames 27 inside the firebox. The side wall burners 26 are arranged in three levels, there being a lower level near the floor of the firebox and then two levels above that. In use, the flow F of gas passes downwardly through the upstream portion UP of the pyrolysis tube 1 where there is no combustion zone, partly into the combustion zone 25, the lower part of the annular swirl flow section 31 being located adjacent to the upper level of side wall burners 26. The flow F then continues downwardly into the swirl flow section 35 which is fully in the combustion zone 25.

It will be seen that in the embodiments of FIGS. 15 to 23, each having an upstream portion UP having an annular swirl flow section 31 and a downstream portion DP having a non-annular flow section (either a conventional flow section 33 or a swirl flow section 35), the internal diameter of the radially outer tubular wall 2 of the annular flow section is greater than the internal diameter of the radially outer wall 2 of the non-annular flow section.

FIGS. 24-29 show variations of designs of pyrolysis tube 1. In all these variations the pyrolysis tube 1 has two upstream portions UP1 and UP2 which feed into a single downstream portion DP. In each case each upstream portion comprises an annular swirl flow section 31. Each downstream portion comprises either a swirl flow section 35 or a conventional flow section 33, i.e. one having a cylindrical radially outer tubular wall with a straight centre line.

Figure 24:
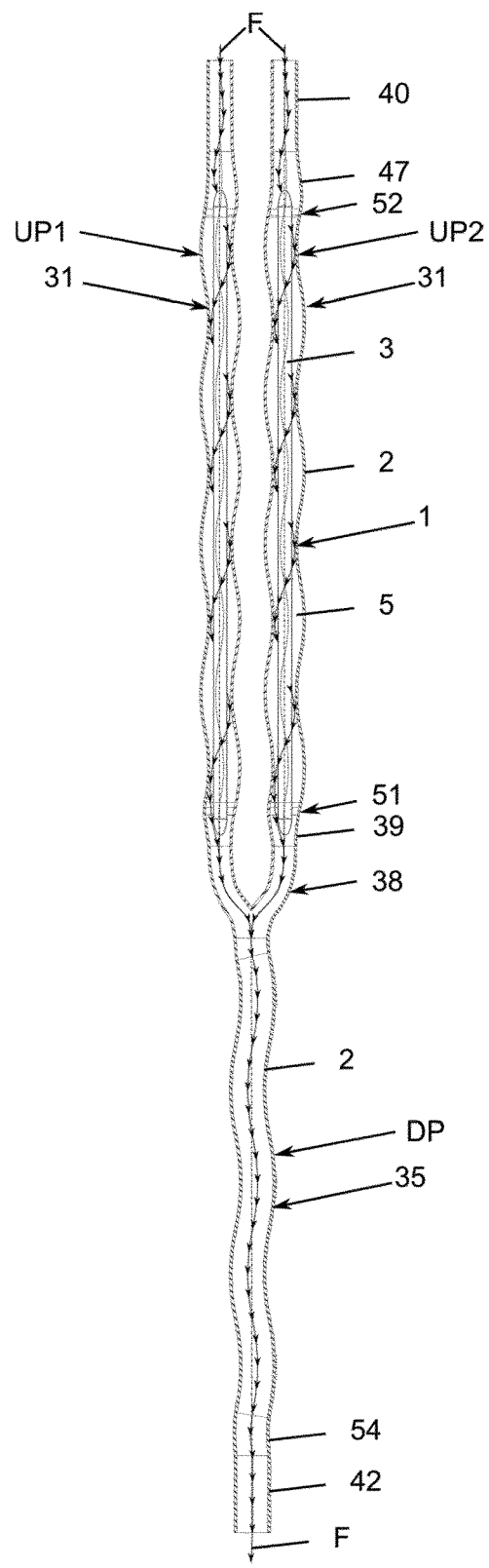
FIGS. 24-29 are schematic longitudinal sectional views through further variations of pyrolysis tube.
Figure 25:
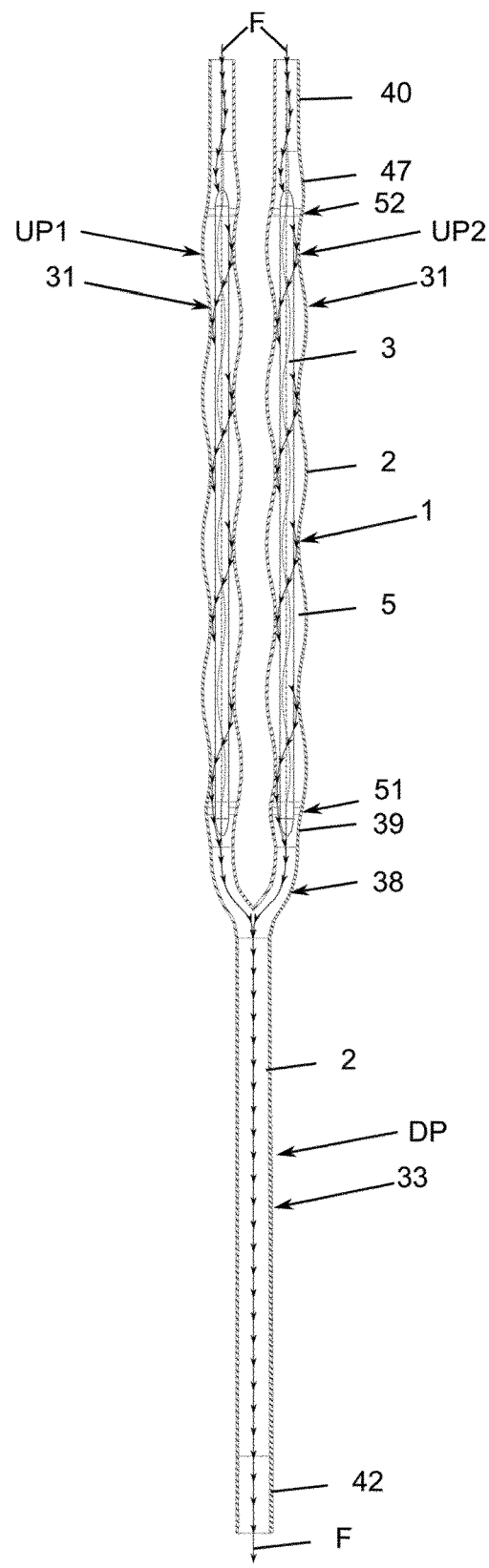

The embodiments of FIGS. 24 and 25 provide for a single pass of a flow F of gas through a cracking furnace. In each case the two upstream portions UP1 and UP2 join at a Y-junction portion 38 where the separate gas flows in each of the two upstream portions unite into a single flow in the downstream portion DP. Each upstream portion is constructed in accordance with the pyrolysis tube design of the second type and have the same features as each other. Each upstream portion UP1, UP2 has an inlet portion 40 at the top, below that a first upper transitional portion 47, and below that an annular swirl flow section 31 providing a flow passage 5 which is a helically winding annular flow passage. At its lower end the annular swirl flow section 31 is connected via a second intermediate transitional portion 39 to the Y-junction portion 38, providing a transition from helical to straight.

The construction of the parts of the two upstream portions UP1 and UP2 which provide the annular flow passage 5 corresponds to that described in relation to FIGS. 8, 9 and 10. A cylindrical inner body 3 is supported inside a helical radially outer tubular wall 2 by a first support arrangement 51 at the lower end of the inner body 3 and a second support arrangement 52 at the upper end of the inner body. More details concerning the support arrangements are explained above in the description of FIGS. 8, 9 and 10. The features of the upstream and downstream portions UP1, UP2 are the same in the embodiments of FIGS. 24 and 25. The downstream portion DP differs between these two embodiments.

In the embodiment of FIG. 24 the downstream portion DP has a helical outer tube 2 so as to provide a swirl flow section 35. The swirl flow section 35 has no inner body and so the passage defined therein is non-annular. The passage has a generally circular cross-sectional shape. A third lower transitional portion 54 is arranged below the swirl flow section 35, between the swirl flow section and a straight outlet portion 42, providing a transition from helical to straight.

In the embodiment of FIG. 25, downstream of the Y-junction portion 38 a conventional flow section 33 is provided, rather than the swirl flow section 35 as shown in FIG. 24. The conventional flow section 33 connects directly to the outlet portion 42.

The embodiments of FIGS. 26, 27, 28 and 29 relate to pyrolysis tubes which provide a dual pass of the flow F through a cracking furnace. In each case the direction of flow is reversed by one or more U-bends from a downward flow direction in the two upstream portions UP1 and UP2 to an upward flow direction in a single downstream portion DP. In each case the two upstream portions UP1, UP2 have annular swirl flow sections 31 with a pyrolysis tube design of the second type. Thus they each have a cylindrical inner body 3, a radially outer tubular wall 2 with a helical configuration, and a flow passage 5 which is a helically winding annular flow passage.

Referring to the embodiment of FIG. 26, the two upstream portions UP1, UP2 have the same construction as each other and therefore only one of them will be described. Each upstream portion UP1, UP2 is provided with a respective inlet portion 40. A first upper transitional portion 47 is located below the inlet portion 40 and joins to an annular swirl flow section 31, i.e. that part of the pyrolysis tube 1 having the helically winding annular flow passage 5. At the lower end of the annular swirl flow section 31 a first lower transitional portion 50 connects to a straight intermediate section 37 which in turn connects to one limb of a U-bend section 36. The U-bend section 36 has another limb which connects to another straight intermediate section 37 and this connects to a Y-junction portion 38. Above the Y-junction portion 38 there is provided a third intermediate transitional portion 41 which connects to a swirl flow section 35 of the downstream portion DP. This provides a transition from a straight part of the Y-junction portion to the helical swirl flow section 35 with its radially outer tubular wall 2 with a helical centre line. A third upper transitional portion 49 is provided between the downstream end of the swirl flow section 35 and an upstream end of an outlet portion 42, to provide a transition from helical to straight.

Figure 26:
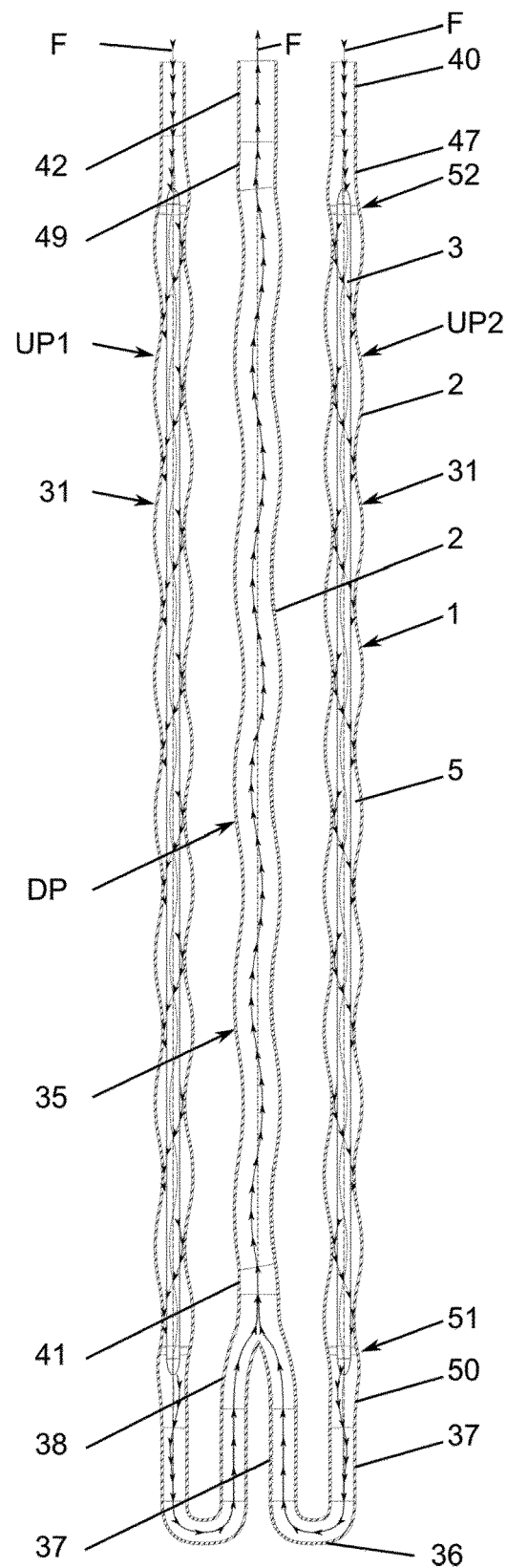
Figure 27:
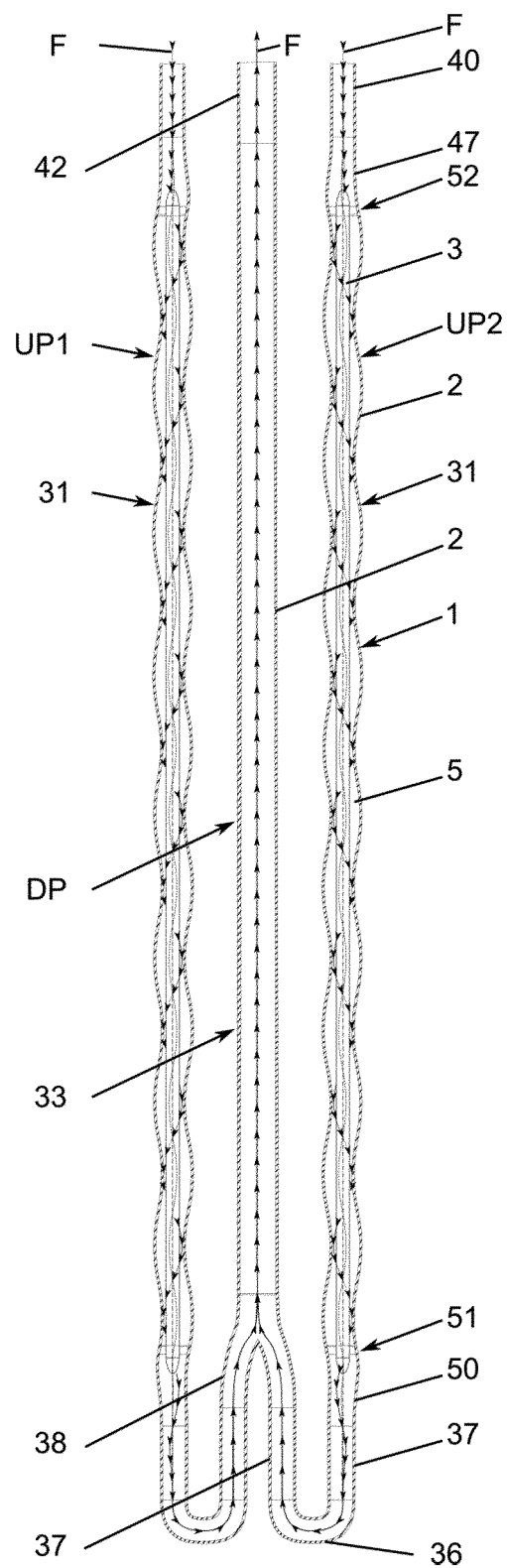

In the embodiment of FIG. 27 the construction of the two upstream portions UP1 and UP2, the lower transitional portions 50, the straight intermediate sections 37, the U-bend sections 36 and the Y-junction portion 38 are the same as those of the equivalent features of the embodiment of FIG. 26 and their description in relation to FIG. 26 is therefore applicable to FIG. 27. The embodiment of FIG. 27 differs from that of FIG. 26 in that the downstream portion DP has a conventional flow section 33 rather than a swirl flow section 35. At its upstream end the conventional flow section 33 is connected directly to the Y-junction portion 38, and at its downstream end it is connected directly to the straight outlet portion 42.

It will be seen that in the embodiments of FIGS. 26 and 27 each of the upstream portions UP1 and UP2 joins via a respective U-bend section 36 to a Y-junction portion 38 where the flows from the respective upstream portions UP1 and UP2 are united. There are two U-bend sections 36 and downstream of that one Y-junction portion 38.

In the pyrolysis tubes of both FIGS. 26 and 27 the downstream portion DP is located between the upstream portions UP1 and UP2. When such a pyrolysis tube is located between burners in a cracking furnace, for example as shown in any of the arrangements of FIGS. 17 to 23, the downstream portion DP is more thermally shielded from the burners than the upstream portions UP1 and UP2. The effect is that the heat input from the furnace is relatively uniform around the circumference of the part of the pyrolysis tube forming the downstream portion DP, rather than being greater where the tube is exposed directly to radiation from the burners and less where it is not so exposed. This design has the advantage that the heat flux profile radially through the wall of the tube on the downstream portion is close to ideal, tending to have a generally similar profile around the circumference of the tube. This reduces the difference between the peak heat flux and the average heat flux such that the difference between the peak tube metal temperature and the average tube metal temperature is minimal, thus prolonging the run length of the pyrolysis tube between decoking operations.

Figure 28:
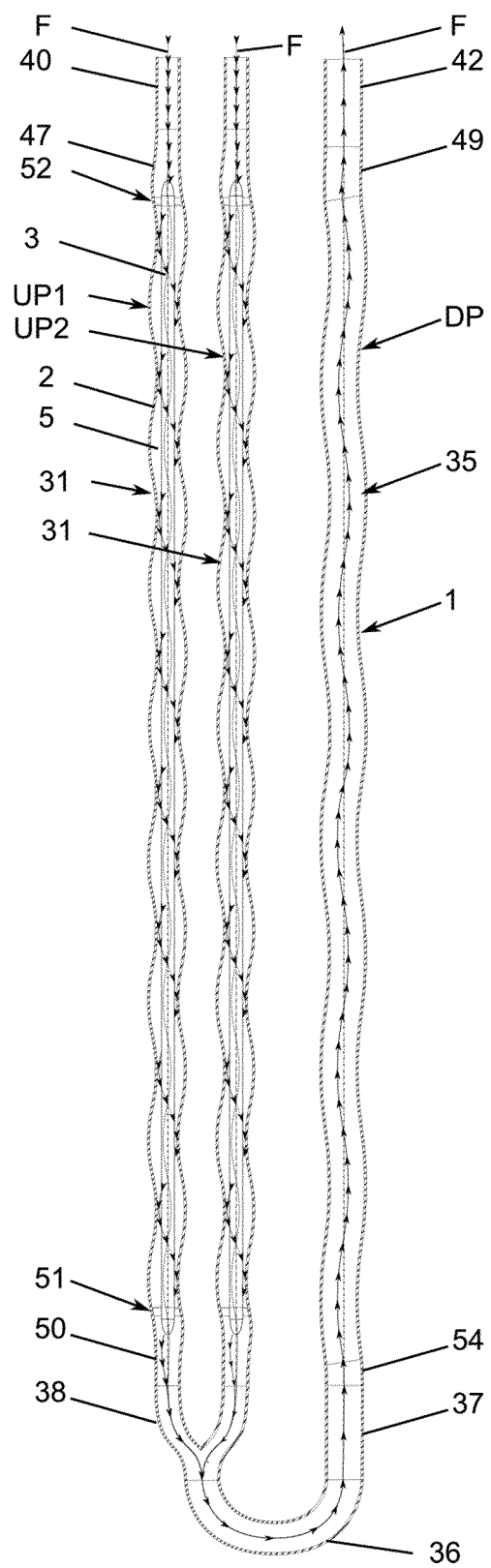
Figure 29:
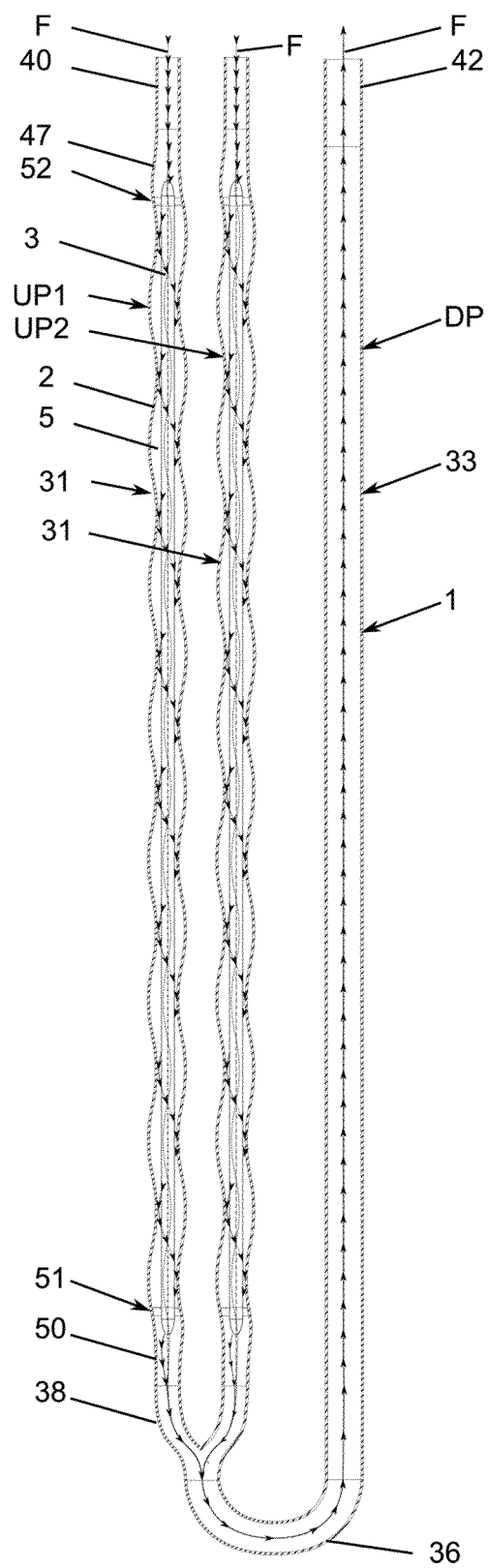

The embodiments of FIGS. 28 and 29 are similar to those of FIGS. 26 and 27, in that there are two upstream portions UP1 and UP2, the outflows from which unite to a single downstream portion DP. In the cases of these embodiments however there is a single U-bend section 36 which is fed by the Y-junction portion 38 which itself is fed via respective first lower transitional portions 50 by the two upstream portions UP1 and UP2. Other than that the constructions of the two upstream portions UP1 and UP2 in the embodiments of FIGS. 28 and 29 are the same as that of the upstream portions UP1 and UP2 of the FIG. 26 embodiment and the description of that is applicable to the FIG. 28 and FIG. 29 embodiments.

Referring to the FIG. 28 embodiment, this has a downstream portion DP comprising a swirl flow section 35, i.e. it has a radially outer tubular wall 2 with a helical centre line. The U-bend section 36 connects to a straight intermediate section 37 which in turn connects to a third lower transitional portion 54. This provides a transition to the swirl flow section 35.

The embodiment of FIG. 29 differs from that of FIG. 28 in that the downstream portion DP is a conventional flow section 33, i.e. it has a cylindrical radially outer tubular wall with a straight centre line. The conventional flow section 33 is connected at its upstream end directly to the U-bend section 36 and at its downstream end directly to a straight outlet portion 42.

The embodiments of FIGS. 15-29 show pyrolysis tubes of the second type, but these pyrolysis tubes could alternatively be of the first type or the third type. Whether of the first second or third type, they could include at least one helical protuberance protruding into the annular flow passage.

In all the embodiments described above, there is a helically winding annular flow passage in which rotation of the gas as it flows along the pyrolysis tube is promoted. The promotion of rotation of the gas flow in the annular flow passage improves heat transfer into the gas. The rotational flow can result in the gas having a radial velocity component on top of the axial velocity component, so-called swirl flow. The swirl flow in the annular passage improves the convective heat transfer, while the inner body serves to create the rotational flow promoting annular flow passage. Because convective heat transfer is improved, a shorter length of pyrolysis tube compared to a conventional one may be used to achieve the same amount of heat transfer into the gas. This in turn achieves a low residence time and improves the yield i.e. the generation of the desired cracked products.

COMPARATIVE EXAMPLES

Reference is made to:
van Goethem, M. W. M., Jelsma, E., 2014. Numerical and experimental study of enhanced heat transfer and pressure drop for high temperature applications;
Chemical Engineering Research and Design 92, 663-671.
This article contains the results of a computational fluid dynamics (CFD) study comparing conventional flow and swirl flow.

For the present specification, a CFD study of annular swirl flow was done on the same basis. A comparison was made between the performance of three types of pyrolysis tube in a cracking furnace. The results are shown in the table below.

| Parameter | Conventional | Swirl Flow | Annular Swirl Flow |
|---|---|---|---|
| Flow rate in kg/hour | 500 | 500 | 500 |
| Outside diameter outer tube in m | 0.06 | 0.064 | 0.089 |
| Inside diameter outer tube in m ($D_o$) | 0.052 | 0.056 | 0.078 |
| Outside diameter inner body in m ($D_i$) | | | 0.047 |
| Length in m | 12.00 | 8.68 | 6.49 |
| Duty | 100% | 100% | 100% |
| Pressure drop | 100% | 100% | 100% |
| Pyrolysis tube length | 100% | 72% | 54% |
| Residence time | 100% | 84% | 77% |

The column headed "Conventional" relates to a conventional pyrolysis tube with a straight centre line.

The column headed "Swirl Flow" relates to a pyrolysis tube of the type known from WO 2010/032024 having a helical centre line and an unobstructed flow lumen, i.e. no inner body. In this case, the amplitude A of the helix was 16.8 mm and the pitch P was 434 mm. It will be seen from the table that the inside diameter $D_O$ of the tube was 56 mm. Thus, the relative amplitude of the helical centre line was $A/D_O$ was 30%. The relative pitch $P/D_O$ was 7.75.

The column headed "Annular Swirl Flow" relates to an embodiment of the present invention based on the third type of pyrolysis tube in which the inner body 3 has a helical centre line and the radially outer tube 2 has a straight centre line. The amplitude A of the helical centre line was 23.4 mm and the pitch P was 605 mm. Thus the relative amplitude $A/D_O$ was 0.3 and the relative pitch $P/D_O$ was 7.75.

It will be noted that in the study certain parameters were set to be the same for all examples. Thus, all the pyrolysis tubes had the same mass flow rate of 500 kg/hour. All tubes are sized such that they have the same 100% "duty". This means that the outside surface temperature of the tube at its outlet from the furnace chamber is greater than the average gas temperature inside the tube at the outlet by the same amount in each example. This temperature difference was 190° C. The average gas inlet temperature to the pyrolysis tube and the average gas outlet temperature were also set as being equal in all cases. Thus the tubes were sized (length and diameter(s)) such that the "duty", i.e. to have the temperature difference at the outlet as described above, is the same in each case.

All tubes have different friction characteristics. In this study the dimensions (length and diameter(s)) were adjusted such that the pressure drop was also the same for all cases. It is then possible to say that the effect that pressure drop has on the yield is identical for all cases.

The result is a table that highlights the effect of the pyrolysis tube geometry on the tube length and the residence time. From the table it can be seen that a pyrolysis tube with a helical centre line (Swirl Flow) results in a reduction in pyrolysis tube length to 72% of that of a conventional pyrolysis tube, and that the residence time is reduced to 84% of that for the conventional pyrolysis tube.

However, the example using an embodiment of the present invention ("Annular Swirl Flow") results in greater reductions of these parameters. The length is reduced by 46%, from 100% to 54%. Importantly, the residence time is reduced by 23% from 100% to 77%. The residence time is the parameter of most interest, because this determines the selectivity of the process. Reduction of the residence time under the same temperature and pressure conditions results in an improvement of the selectivity towards the primary cracking products, i.e. ethylene, propylene, butadiene.

The invention claimed is:

1. A cracking furnace comprising a pyrolysis tube for carrying a flow of fluid, the pyrolysis tube comprising a radially inner body having a radially outermost peripheral portion extending circumferentially of the radially inner body, and a radially outer wall having a radially inwardly facing surface, the radially outermost peripheral portion of the radially inner body and the radially inwardly facing surface of the radially outer wall together defining an annular flow passage, wherein at least one of the radially inner body and the radially outer wall has a centre line which extends helically in a longitudinal direction of the pyrolysis tube, so as to promote rotation of the fluid as it flows along the pyrolysis tube, and wherein at least one support is provided to support the radially inner body with the radially outermost peripheral portion of the radially inner body being radially inwardly spaced from the radially inwardly facing surface of the radially outer wall around the circumference of the radially outermost peripheral portion, so as to provide said annular flow passage radially outwardly of the radially outermost peripheral portion.

2. A cracking furnace as claimed in claim 1, wherein the pyrolysis tube comprises a non-annular flow passage defined by a radially outer wall downstream of the annular flow passage.

3. A cracking furnace as claimed in claim 2, wherein the radially outer wall of the non-annular flow passage has a centre line which extends helically in a longitudinal direction of the pyrolysis tube.

4. A cracking furnace as claimed in claim 2, wherein the radially outer wall of the non-annular flow passage has a straight centre line in a longitudinal direction of the pyrolysis tube.

5. A cracking furnace as claimed in claim 2, wherein the radially outer wall of the annular flow passage has an internal diameter which is greater than an internal diameter of the radially outer wall of the non-annular flow passage.

6. A cracking furnace as claimed in claim 2, wherein the pyrolysis tube comprises a plurality of branches each having a respective radially inner body and a respective radially outer wall which together define a respective annular flow passage, at least one of the radially inner body and the radially outer wall of each branch being configured to promote rotation of the fluid flow, the branches joining together at a junction and the non-annular flow passage being provided downstream of the junction.

7. A cracking furnace as claimed in claim 1, comprising at least one burner in a firing region of the cracking furnace where the pyrolysis tube extends, and wherein the pyrolysis tube extends in the furnace downstream away from said firing region.

8. A cracking furnace as claimed in claim 1, wherein the pyrolysis tube extends downwardly from an inlet thereto.

9. A cracking furnace as claimed in claim 1, wherein the inner body is hollow.

10. A cracking furnace as claimed in claim 1, wherein both the radially inner body and the radially outer wall have respective centre lines which extend helically in a longitudinal direction of the pyrolysis tube, wherein the centre lines are coincident.

11. A cracking furnace as claimed in claim 10, wherein the width of the annular flow passage measured perpendicularly to the longitudinal direction of the pyrolysis tube is less than or equal to 25% of the diameter of the radially outer tube.

12. A cracking furnace as claimed in claim 1, wherein the width of the annular flow passage measured perpendicularly to the longitudinal direction of the pyrolysis tube varies in the circumferential direction of the tube.

13. A cracking furnace as claimed in claim 1, wherein the radially inner body has a straight centre line and the radially outer wall has a centre line which extends helically.

14. A cracking furnace as claimed in claim 1, wherein the radially inner body has a centre line which extends helically and the radially outer wall has a straight centre line.

15. A cracking furnace as claimed in claim 1, wherein a maximum width of the annular flow passage measured perpendicularly to the longitudinal direction of the pyrolysis tube is less than or equal to half the diameter of the radially outer tube.

16. A cracking furnace as claimed in claim 1, wherein longitudinally spaced apart supports are provided to support the inner body in the pyrolysis tube, a first such support being fixed to the radially outer wall and the inner body, and the second such support comprising at least one support member fixed to the radially outer wall and positioned radially outwardly of the inner body but not fixed thereto.

17. A cracking furnace as claimed in claim 1, wherein the pyrolysis tube provides a dual pass of the flow through the cracking furnace and comprises an upstream portion in a first pass and a downstream portion in a second pass, and wherein the downstream portion is at least to some extent in the shadow of the upstream portion with respect to a burner of the cracking furnace.

18. A cracking furnace as claimed in claim 1, wherein the radially inner body and/or the radially outer wall has at least one helical protuberance protruding into the annular flow passage.

19. A method of cracking a hydrocarbon feedstock to produce cracked products, comprising feeding the hydrocarbon feedstock into a pyrolysis tube of a cracking furnace, the pyrolysis tube comprising a radially inner body having a radially outermost peripheral portion extending circumferentially of the radially inner body, and a radially outer wall having a radially inwardly facing surface, the radially outermost peripheral portion of the radially inner body and the radially inwardly facing surface of the radially outer wall together defining an annular flow passage, wherein at least one of the radially inner body and the radially outer wall has a centre line which extends helically in a longitudinal direction of the pyrolysis tube, so as to promote rotation of the fluid as it flows along the pyrolysis tube, and wherein at least one support is provided to support the radially inner body with the radially outermost peripheral portion of the radially inner body being radially inwardly spaced from the radially inwardly facing surface of the radially outer wall around the circumference of the radially outermost peripheral portion, so as to provide said annular flow passage radially outwardly of the radially outermost peripheral portion.

20. A cracking furnace comprising a pyrolysis tube for carrying a flow of fluid, the pyrolysis tube comprising a radially inner body and a radially outer wall which together define an annular flow passage, wherein the cracking furnace comprises one of:
 (1) the radially inner body and the radially outer wall each having respective centre lines which extend helically in a longitudinal direction of the pyrolysis tube, so as to promote rotation of the fluid as it flows along the pyrolysis tube; and
 (2) the radially outer wall having a centre line which extends helically in a longitudinal direction of the pyrolysis tube, so as to promote rotation of the fluid as it flows along the pyrolysis tube; and
 (3) the radially inner body having a main body which has a centre line which extends helically in a longitudinal direction of the pyrolysis tube, so as to promote rotation of the fluid as it flows along the pyrolysis tube, the main body having a circular cross section in a plane perpendicular to the helical centre line.

\* \* \* \* \*